US009623260B2

(12) United States Patent
White et al.

(10) Patent No.: US 9,623,260 B2
(45) Date of Patent: *Apr. 18, 2017

(54) EXPANDABLE BRACHYTHERAPY DEVICE

(71) Applicant: THERAGENICS CORPORATION, Buford, GA (US)

(72) Inventors: Jack C. White, Alpharetta, GA (US); David Wesley Stephens, Cornelia, GA (US); Amit Prakash Govil, Gainesville, FL (US); Joshua J. Bergman, Myrtle Point, OR (US); Nathan Christopher Griffith, Lawrenceville, GA (US); Kyle Kevin Millage, Flemington, NJ (US)

(73) Assignee: Theragenics Corporation, Buford, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/861,195

(22) Filed: Apr. 11, 2013

(65) Prior Publication Data

US 2013/0225902 A1    Aug. 29, 2013

Related U.S. Application Data

(63) Continuation of application No. 12/775,636, filed on May 7, 2010, now Pat. No. 8,562,504, which is a
(Continued)

(51) Int. Cl.
*A61N 5/10* (2006.01)
*A61M 29/02* (2006.01)

(52) U.S. Cl.
CPC .......... *A61N 5/1015* (2013.01); *A61M 29/02* (2013.01); *A61N 5/1007* (2013.01);
(Continued)

(58) Field of Classification Search
CPC .......... A61N 2005/1018; A61N 5/1015; A61N 2005/1005; A61N 2005/1024; A61N 5/1007
(Continued)

(56) References Cited

U.S. PATENT DOCUMENTS 3,060,924 A   10/1962   Rush
3,324,847 A    6/1967   Zoumboulis
(Continued)

FOREIGN PATENT DOCUMENTS

CA    2037056    1/1991
DE    2539553    3/1977
(Continued)

OTHER PUBLICATIONS

XP007904995:retrieved from the Internet: URL: http://www2.dupont.com/Teflon_Industrial/en_US/assets/downloads/h88800.pdf; retrieved on Jun. 19, 2008, by Authorized Officer in International Application PCT/US2008/003364.
(Continued)

*Primary Examiner* — Christine H Matthews
(74) *Attorney, Agent, or Firm* — Mendelsohn Dunleavy, P.C.

(57) ABSTRACT

A method for brachytherapy in a lumpectomy cavity of a breast including, positioning a distal end of a brachytherapy device within the cavity, expanding an expandable surface portion located between proximal and distal ends of the device within the cavity, the source lumen tubes defining a curved configuration within the cavity; and positioning a source of radiation sequentially within one or more source lumens of the source lumen tubes according to a brachytherapy treatment plan. The device includes an inner tube, and a plurality of source lumen tubes located around the inner tube and including distal ends secured together with
(Continued)

the inner tube at the distal end disposed within the body cavity, the source lumen tubes comprising proximal portions sufficiently long to extend outside the breast.

23 Claims, 16 Drawing Sheets

Related U.S. Application Data continuation of application No. 12/493,884, filed on Jun. 29, 2009, now Pat. No. 8,690,746, which is a continuation of application No. 11/266,994, filed on Nov. 4, 2005, now Pat. No. 7,662,082.

(60) Provisional application No. 60/625,355, filed on Nov. 5, 2004.

(52) U.S. Cl.
CPC .................. *A61N 2005/1008* (2013.01); *A61N 2005/1018* (2013.01); *A61N 2005/1024* (2013.01)

(58) Field of Classification Search
USPC ............................................ 600/1–8; 604/21
See application file for complete search history.

(56) References Cited

U.S. PATENT DOCUMENTS

| | | |
|---|---|---|
| 3,502,878 A | 3/1970 | Stewart |
| 3,750,653 A | 8/1973 | Simon |
| 3,863,073 A | 1/1975 | Wagner |
| 3,872,856 A | 3/1975 | Clayton |
| 3,968,803 A | 7/1976 | Hymann |
| 3,971,950 A | 7/1976 | Evans et al. |
| 3,975,350 A | 8/1976 | Hudgin et al. |
| 4,119,094 A | 10/1978 | Micklus et al. |
| 4,160,906 A | 7/1979 | Daniels et al. |
| 4,310,766 A | 1/1982 | Finkenzeller et al. |
| 4,350,169 A | 9/1982 | Dutcher et al. |
| 4,417,576 A | 11/1983 | Baran |
| 4,427,005 A | 1/1984 | Tener |
| 4,454,106 A | 6/1984 | Gansow et al. |
| 4,496,557 A | 1/1985 | Malen et al. |
| 4,559,641 A | 12/1985 | Caugant et al. |
| 4,571,241 A | 2/1986 | Christopher |
| 4,580,561 A | 4/1986 | Williamson |
| 4,690,677 A | 9/1987 | Erb |
| 4,706,269 A | 11/1987 | Reina et al. |
| 4,706,652 A | 11/1987 | Horowitz |
| 4,714,074 A | 12/1987 | Rey et al. |
| 4,744,099 A | 5/1988 | Huettenrauch et al. |
| 4,754,745 A | 7/1988 | Horowitz |
| 4,763,642 A | 8/1988 | Horowitz |
| 4,773,086 A | 9/1988 | Fujita et al. |
| 4,773,087 A | 9/1988 | Plewes |
| 4,798,212 A | 1/1989 | Arana |
| 4,819,258 A | 4/1989 | Kleinman et al. |
| 4,821,725 A | 4/1989 | Azam et al. |
| 4,821,727 A | 4/1989 | Levene et al. |
| 4,867,741 A | 9/1989 | Portnoy |
| 4,929,470 A | 5/1990 | Rittenhouse et al. |
| 4,936,823 A | 6/1990 | Colvin et al. |
| 4,953,558 A | 9/1990 | Akerfeldt |
| 4,957,476 A | 9/1990 | Cano |
| 4,969,174 A | 11/1990 | Scheid et al. |
| 4,976,680 A | 12/1990 | Hayman et al. |
| 4,989,227 A | 1/1991 | Tirelli et al. |
| 4,998,917 A | 3/1991 | Gaiser et al. |
| 4,998,930 A | 3/1991 | Lundahl |
| 5,015,247 A | 5/1991 | Michaelson |
| 5,018,176 A | 5/1991 | Romeas et al. |
| 5,025,797 A | 6/1991 | Baran |
| RE33,634 E | 7/1991 | Yanaki |
| 5,029,193 A | 7/1991 | Saffer |
| 5,051,904 A | 9/1991 | Griffith |
| 5,056,523 A | 10/1991 | Hotchkiss et al. |
| 5,059,166 A | 10/1991 | Fischell et al. |
| 5,078,142 A | 1/1992 | Siczek et al. |
| 5,084,001 A | 1/1992 | Vant Hooft et al. |
| 5,084,015 A | 1/1992 | Moriuchi |
| 5,084,022 A | 1/1992 | Claude |
| 5,106,360 A | 4/1992 | Ishiwara et al. |
| 5,112,303 A | 5/1992 | Pudenz et al. |
| 5,152,741 A | 10/1992 | Farnio |
| 5,152,747 A | 10/1992 | Olivier |
| 5,163,075 A | 11/1992 | Lubinsky et al. |
| 5,164,976 A | 11/1992 | Scheid et al. |
| 5,167,622 A | 12/1992 | Muto |
| 5,199,056 A | 3/1993 | Darrah |
| 5,199,939 A | 4/1993 | Dake et al. |
| 5,227,969 A | 7/1993 | Waggener et al. |
| 5,235,966 A | 8/1993 | Jamner |
| 5,236,410 A | 8/1993 | Granov et al. |
| 5,240,011 A | 8/1993 | Assa |
| 5,242,372 A | 9/1993 | Carol |
| 5,259,847 A | 11/1993 | Trambert |
| 5,279,565 A | 1/1994 | Klein et al. |
| 5,289,520 A | 2/1994 | Pellegrino et al. |
| 5,302,168 A | 4/1994 | Hess |
| 5,312,356 A | 5/1994 | Engelson et al. |
| 5,314,518 A | 5/1994 | Ito et al. |
| 5,336,178 A | 8/1994 | Kaplan et al. |
| 5,342,305 A | 8/1994 | Shonk |
| 5,354,257 A | 10/1994 | Roubin et al. |
| 5,359,637 A | 10/1994 | Webber |
| 5,365,562 A | 11/1994 | Toker |
| 5,381,504 A | 1/1995 | Novack et al. |
| 5,411,466 A | 5/1995 | Hess |
| 5,415,169 A | 5/1995 | Siczek et al. |
| 5,417,687 A | 5/1995 | Nardella et al. |
| 5,422,926 A | 6/1995 | Smith et al. |
| 5,423,747 A | 6/1995 | Amano |
| 5,426,685 A | 6/1995 | Pellegrino et al. |
| 5,428,658 A | 6/1995 | Oettinger et al. |
| 5,429,582 A | 7/1995 | Williams |
| 5,429,605 A | 7/1995 | Richling et al. |
| 5,452,367 A | 9/1995 | Bick et al. |
| 5,476,101 A | 12/1995 | Schramm et al. |
| 5,484,384 A | 1/1996 | Fearnot |
| 5,503,613 A | 4/1996 | Weinberger |
| 5,506,877 A | 4/1996 | Niklason et al. |
| 5,507,298 A | 4/1996 | Schramm et al. |
| 5,509,900 A | 4/1996 | Kirkman |
| 5,520,646 A | 5/1996 | D'Andrea |
| 5,526,394 A | 6/1996 | Siczek et al. |
| 5,535,817 A | 7/1996 | Dunne |
| 5,538,502 A | 7/1996 | Johnstone |
| 5,539,797 A | 7/1996 | Heidsieck et al. |
| 5,540,659 A | 7/1996 | Teirstein |
| 5,553,111 A | 9/1996 | Moore et al. |
| 5,562,594 A | 10/1996 | Weeks |
| 5,566,221 A | 10/1996 | Smith et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,603,991 A | 2/1997 | Kupiecki et al. |
| 5,609,152 A | 3/1997 | Pellegrino et al. |
| 5,611,767 A | 3/1997 | Williams |
| 5,616,114 A | 4/1997 | Thornton et al. |
| 5,621,780 A | 4/1997 | Smith et al. |
| 5,624,395 A | 4/1997 | Mikhail et al. |
| 5,627,869 A | 5/1997 | Andrew et al. |
| 5,653,683 A | 8/1997 | D'Andrea |
| 5,657,362 A | 8/1997 | Giger et al. |
| 5,662,580 A | 9/1997 | Bradshaw et al. |
| 5,668,889 A | 9/1997 | Hara |
| 5,678,572 A | 10/1997 | Shaw et al. |
| 5,704,926 A | 1/1998 | Sutton |
| 5,706,327 A | 1/1998 | Adamkowski et al. |
| 5,719,952 A | 2/1998 | Rooks |

(56) References Cited

U.S. PATENT DOCUMENTS

| | | | |
|---|---|---|---|
| 5,720,717 A * | 2/1998 | D'Andrea | .................. 604/21 |
| 5,724,400 A | 3/1998 | Swerdloff et al. | |
| 5,730,698 A | 3/1998 | Fischell et al. | |
| 5,735,264 A | 4/1998 | Siczek et al. | |
| 5,741,253 A | 4/1998 | Michaelson | |
| 5,759,173 A | 6/1998 | Preissman et al. | |
| 5,769,086 A | 6/1998 | Ritchart et al. | |
| 5,782,740 A | 7/1998 | Schneiderman | |
| 5,782,742 A | 7/1998 | Crocker et al. | |
| 5,800,333 A | 9/1998 | Liprie | |
| 5,803,895 A | 9/1998 | Kronholz et al. | |
| 5,803,912 A | 9/1998 | Siczek et al. | |
| 5,818,898 A | 10/1998 | Tsukamoto et al. | |
| 5,820,594 A | 10/1998 | Fontirroche et al. | |
| 5,820,717 A | 10/1998 | Siegenthaler | |
| 5,828,722 A | 10/1998 | Ploetz et al. | |
| 5,840,008 A | 11/1998 | Klein et al. | |
| 5,843,163 A | 12/1998 | Wall | |
| 5,851,171 A | 12/1998 | Gasson | |
| 5,851,182 A | 12/1998 | Sahadevan | |
| 5,863,284 A | 1/1999 | Klein | |
| 5,863,285 A | 1/1999 | Coletti | |
| 5,872,828 A | 2/1999 | Niklason et al. | |
| 5,878,104 A | 3/1999 | Ploetz | |
| 5,882,291 A | 3/1999 | Bradshaw et al. | |
| 5,891,091 A | 4/1999 | Teirstein | |
| 5,896,437 A | 4/1999 | Ploetz | |
| 5,899,882 A | 5/1999 | Waksman et al. | |
| 5,908,406 A | 6/1999 | Ostapchenko et al. | |
| 5,910,102 A | 6/1999 | Hastings | |
| 5,913,813 A | 6/1999 | Williams et al. | |
| 5,916,143 A | 6/1999 | Apple et al. | |
| 5,919,473 A | 7/1999 | Elkhoury | |
| 5,924,973 A | 7/1999 | Weinberger | |
| 5,931,774 A | 8/1999 | Williams et al. | |
| 5,935,098 A | 8/1999 | Blaisdell et al. | |
| 5,938,582 A | 8/1999 | Ciamacco et al. | |
| 5,942,209 A | 8/1999 | Leavitt et al. | |
| 5,976,106 A | 11/1999 | Verin et al. | |
| 5,986,662 A | 11/1999 | Argiro et al. | |
| 5,989,197 A | 11/1999 | Avaltroni | |
| 5,993,972 A | 11/1999 | Reich et al. | |
| 6,005,907 A | 12/1999 | Ploetz | |
| 6,013,019 A | 1/2000 | Fischell et al. | |
| 6,022,308 A | 2/2000 | Williams | |
| 6,022,325 A | 2/2000 | Siczek et al. | |
| 6,030,333 A | 2/2000 | Sioshansi et al. | |
| 6,033,357 A | 3/2000 | Ciezki et al. | |
| 6,036,631 A | 3/2000 | McGrath et al. | |
| 6,036,632 A | 3/2000 | Whitmore et al. | |
| 6,050,930 A | 4/2000 | Teirstein | |
| 6,056,722 A | 5/2000 | Jayaraman | |
| 6,059,752 A | 5/2000 | Segal | |
| 6,071,263 A | 6/2000 | Kirkman | |
| 6,074,339 A | 6/2000 | Gambale et al. | |
| 6,075,879 A | 6/2000 | Roehrig et al. | |
| 6,083,148 A | 7/2000 | Williams | |
| 6,086,970 A | 7/2000 | Ren | |
| 6,091,841 A | 7/2000 | Rogers et al. | |
| 6,093,142 A | 7/2000 | Ciamacco, Jr. | |
| 6,095,966 A | 8/2000 | Chornenky et al. | |
| 6,117,064 A | 9/2000 | Apple et al. | |
| 6,137,527 A | 10/2000 | Abdel-Malek et al. | |
| 6,141,398 A | 10/2000 | He et al. | |
| 6,143,013 A | 11/2000 | Samson et al. | |
| 6,149,301 A | 11/2000 | Kautzer et al. | |
| 6,159,139 A | 12/2000 | Chiu | |
| 6,159,141 A | 12/2000 | Apple et al. | |
| 6,175,117 B1 | 1/2001 | Komardin et al. | |
| 6,176,821 B1 | 1/2001 | Crocker et al. | |
| 6,179,766 B1 | 1/2001 | Dickerson | |
| 6,196,715 B1 | 3/2001 | Nambu et al. | |
| 6,196,996 B1 | 3/2001 | Teirstein | |
| 6,200,256 B1 | 3/2001 | Weinberger | |
| 6,200,257 B1 | 3/2001 | Winkler | |
| 6,213,976 B1 | 4/2001 | Trerotola | |
| 6,216,540 B1 | 4/2001 | Nelson et al. | |
| 6,217,565 B1 | 4/2001 | Cohen | |
| 6,217,585 B1 | 4/2001 | Houser et al. | |
| 6,219,059 B1 | 4/2001 | Argiro | |
| 6,221,030 B1 | 4/2001 | Avaltroni | |
| 6,233,473 B1 | 5/2001 | Shepherd et al. | |
| 6,234,951 B1 | 5/2001 | Hastings | |
| 6,234,952 B1 | 5/2001 | Liprie | |
| 6,238,374 B1 | 5/2001 | Winkler | |
| 6,243,441 B1 | 6/2001 | Zur | |
| 6,251,059 B1 | 6/2001 | Apple et al. | |
| 6,256,370 B1 | 7/2001 | Yavuz | |
| 6,256,529 B1 | 7/2001 | Holupka et al. | |
| 6,258,099 B1 | 7/2001 | Mareiro et al. | |
| 6,264,599 B1 | 7/2001 | Slater et al. | |
| 6,264,631 B1 | 7/2001 | Willis et al. | |
| 6,267,775 B1 | 7/2001 | Clerc et al. | |
| 6,272,207 B1 | 8/2001 | Tang | |
| 6,282,142 B1 | 8/2001 | Miyawaki | |
| 6,287,249 B1 | 9/2001 | Tam et al. | |
| 6,289,235 B1 | 9/2001 | Webber et al. | |
| 6,292,530 B1 | 9/2001 | Yavus et al. | |
| 6,306,074 B1 | 10/2001 | Waksman et al. | |
| 6,319,188 B1 | 11/2001 | Lovoi | |
| 6,327,336 B1 | 12/2001 | Gingold et al. | |
| 6,338,709 B1 | 1/2002 | Geoffrion et al. | |
| 6,341,156 B1 | 1/2002 | Baetz et al. | |
| 6,371,904 B1 | 4/2002 | Sirimanne et al. | |
| 6,375,352 B1 | 4/2002 | Hewes et al. | |
| 6,378,137 B1 | 4/2002 | Hassan et al. | |
| 6,390,967 B1 | 5/2002 | Forman et al. | |
| 6,390,968 B1 | 5/2002 | Harmon | |
| 6,390,992 B1 | 5/2002 | Morris et al. | |
| 6,398,708 B1 | 6/2002 | Hastings et al. | |
| 6,411,836 B1 | 6/2002 | Patel et al. | |
| 6,413,203 B1 | 7/2002 | Sahatjian | |
| 6,413,204 B1 | 7/2002 | Winkler et al. | |
| 6,415,015 B2 | 7/2002 | Nicolas et al. | |
| 6,416,457 B1 | 7/2002 | Urick et al. | |
| 6,416,492 B1 | 7/2002 | Nielson | |
| 6,428,486 B2 | 8/2002 | Ritchart et al. | |
| 6,442,288 B1 | 8/2002 | Haerer et al. | |
| 6,458,069 B1 | 10/2002 | Tam et al. | |
| 6,458,070 B1 | 10/2002 | Waksman et al. | |
| 6,459,925 B1 | 10/2002 | Nields et al. | |
| 6,482,142 B1 | 11/2002 | Winkler et al. | |
| 6,494,824 B1 | 12/2002 | Apple et al. | |
| 6,501,819 B2 | 12/2002 | Unger et al. | |
| 6,506,145 B1 | 1/2003 | Bradshaw et al. | |
| 6,508,784 B1 | 1/2003 | Shu | |
| 6,512,942 B1 | 1/2003 | Burdette et al. | |
| 6,527,692 B1 | 3/2003 | Weinberger | |
| 6,527,693 B2 | 3/2003 | Munro, III et al. | |
| 6,537,194 B1 | 3/2003 | Winkler | |
| 6,540,655 B1 | 4/2003 | Chin et al. | |
| 6,540,656 B2 | 4/2003 | Fontayne et al. | |
| 6,540,734 B1 | 4/2003 | Chiu et al. | |
| 6,556,655 B1 | 4/2003 | Chichereau et al. | |
| 6,558,390 B2 | 5/2003 | Cragg | |
| 6,579,221 B1 | 6/2003 | Peterson | |
| 6,582,353 B1 | 6/2003 | Hastings et al. | |
| 6,589,158 B2 | 7/2003 | Winkler | |
| 6,592,548 B2 | 7/2003 | Jayaraman | |
| 6,597,762 B1 | 7/2003 | Ferrant et al. | |
| 6,605,030 B2 | 8/2003 | Weinberger | |
| 6,607,476 B1 | 8/2003 | Barnhart | |
| 6,607,477 B1 | 8/2003 | Longton et al. | |
| 6,607,478 B2 | 8/2003 | Williams | |
| 6,610,013 B1 | 8/2003 | Fenster et al. | |
| 6,611,575 B1 | 8/2003 | Alyassin et al. | |
| 6,615,070 B1 | 9/2003 | Lee | |
| 6,616,629 B1 | 9/2003 | Verin et al. | |
| 6,620,111 B2 | 9/2003 | Stephens et al. | |
| 6,626,849 B2 | 9/2003 | Huitema et al. | |
| 6,633,674 B1 | 10/2003 | Barnes et al. | |
| 6,635,008 B1 | 10/2003 | Liprie | |
| 6,638,235 B2 | 10/2003 | Miller et al. | |
| 6,641,518 B2 | 11/2003 | Wolfson et al. | |

(56) References Cited

U.S. PATENT DOCUMENTS

| | | |
|---|---|---|
| 6,645,135 B1 | 11/2003 | Bhat |
| 6,647,092 B2 | 11/2003 | Eberhard et al. |
| 6,659,933 B2 | 12/2003 | Asano |
| 6,673,006 B2 | 1/2004 | Winkler |
| 6,676,667 B2 | 1/2004 | Mareiro et al. |
| 6,685,618 B2 | 2/2004 | Tam et al. |
| 6,692,460 B1 | 2/2004 | Jayaraman |
| 6,699,170 B1 | 3/2004 | Crocker et al. |
| 6,706,014 B2 | 3/2004 | Banik et al. |
| 6,723,052 B2 | 4/2004 | Mills |
| 6,744,848 B2 | 6/2004 | Stanton et al. |
| 6,746,392 B2 | 6/2004 | Stiger et al. |
| 6,746,465 B2 | 6/2004 | Diederich et al. |
| 6,748,044 B2 | 6/2004 | Sabol et al. |
| 6,749,555 B1 | 6/2004 | Winkler et al. |
| 6,749,595 B1 | 6/2004 | Murphy |
| 6,751,285 B2 | 6/2004 | Eberhard et al. |
| 6,752,752 B2 | 6/2004 | Geitz |
| 6,758,824 B1 | 7/2004 | Miller et al. |
| 6,770,058 B1 | 8/2004 | Liprie |
| 6,813,334 B2 | 11/2004 | Koppe et al. |
| 6,882,700 B2 | 4/2005 | Wang et al. |
| 6,885,724 B2 | 4/2005 | Li et al. |
| 6,910,999 B2 | 6/2005 | Chin et al. |
| 6,912,319 B1 | 6/2005 | Barnes et al. |
| 6,913,600 B2 | 7/2005 | Valley et al. |
| 6,923,754 B2 | 8/2005 | Lubock |
| 6,940,943 B2 | 9/2005 | Claus et al. |
| 6,955,641 B2 | 10/2005 | Lubock |
| 6,970,531 B2 | 11/2005 | Eberhard et al. |
| 6,978,040 B2 | 12/2005 | Berestov |
| 6,983,754 B1 | 1/2006 | Anderson et al. |
| 6,987,831 B2 | 1/2006 | Ning |
| 6,999,554 B2 | 2/2006 | Mertelmeier |
| 7,041,047 B2 | 5/2006 | Gellman et al. |
| 7,056,276 B2 | 6/2006 | Nakano et al. |
| 7,098,463 B2 | 8/2006 | Adamovics |
| 7,107,089 B2 | 9/2006 | Lee |
| 7,110,490 B2 | 9/2006 | Eberhard et al. |
| 7,110,502 B2 | 9/2006 | Tsuji |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,171,255 B2 | 1/2007 | Holupka et al. |
| 7,182,725 B2 | 2/2007 | Bonan et al. |
| 7,201,715 B2 | 4/2007 | Burdette et al. |
| 7,214,178 B2 | 5/2007 | Lubock |
| 7,245,694 B2 | 7/2007 | Jing et al. |
| 7,315,607 B2 | 1/2008 | Ramsauer |
| 7,319,735 B2 | 1/2008 | Defreitas |
| 7,322,929 B2 | 1/2008 | Lovoi |
| 7,323,692 B2 | 1/2008 | Rowlands et al. |
| 7,357,770 B1 | 4/2008 | Cutrer et al. |
| 7,404,791 B2 | 7/2008 | Linares et al. |
| 7,407,476 B2 | 8/2008 | Lubock et al. |
| 7,413,539 B2 | 8/2008 | Lubock et al. |
| 7,430,272 B2 | 9/2008 | Jing et al. |
| 7,443,949 B2 | 10/2008 | Defreitas et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,609,806 B2 | 10/2009 | Defreitas et al. |
| 7,630,533 B2 | 12/2009 | Ruth et al. |
| 7,662,082 B2 | 2/2010 | White et al. |
| 7,697,660 B2 | 4/2010 | Ning |
| 7,783,006 B2 | 8/2010 | Stewart et al. |
| 7,792,245 B2 | 9/2010 | Hitzke et al. |
| 7,869,563 B2 | 1/2011 | Defreitas et al. |
| 7,885,382 B2 | 2/2011 | Stewart et al. |
| 7,887,476 B2 | 2/2011 | Hermann et al. |
| 8,075,469 B2 | 12/2011 | Lubock et al. |
| 8,079,946 B2 | 12/2011 | Lubock et al. |
| 8,137,256 B2 | 3/2012 | Cutrer et al. |
| 8,192,344 B2 | 6/2012 | Lubock et al. |
| 8,277,370 B2 | 10/2012 | Quick |
| 8,287,442 B2 | 10/2012 | Quick |
| 8,398,534 B2 | 3/2013 | White et al. |
| 8,562,504 B2 | 10/2013 | White et al. |
| 8,565,374 B2 | 10/2013 | Defreitas et al. |
| 8,568,284 B2 | 10/2013 | White et al. |
| 9,180,312 B2 | 11/2015 | Lubock et al. |
| 9,248,311 B2 | 2/2016 | Damarati |
| 2001/0007071 A1 | 7/2001 | Koblish |
| 2001/0016725 A1 | 8/2001 | Valley et al. |
| 2001/0038681 A1 | 11/2001 | Stanton et al. |
| 2001/0038861 A1 | 11/2001 | Hsu et al. |
| 2001/0049464 A1 | 12/2001 | Ganz |
| 2001/0051669 A1 | 12/2001 | McGhee |
| 2002/0012450 A1 | 1/2002 | Tsujii |
| 2002/0016583 A1 | 2/2002 | Cragg |
| 2002/0026090 A1 | 2/2002 | Kaplan et al. |
| 2002/0032359 A1 | 3/2002 | Geoffrion et al. |
| 2002/0045893 A1 | 4/2002 | Lane et al. |
| 2002/0050986 A1 | 5/2002 | Inoue et al. |
| 2002/0055666 A1 | 5/2002 | Hunter et al. |
| 2002/0075997 A1 | 6/2002 | Unger et al. |
| 2002/0095114 A1 | 7/2002 | Palasis |
| 2002/0156342 A1 | 10/2002 | Burton et al. |
| 2002/0165427 A1 | 11/2002 | Yachia et al. |
| 2002/0177804 A1 | 11/2002 | Saab |
| 2003/0018272 A1 | 1/2003 | Treado et al. |
| 2003/0073895 A1 | 4/2003 | Nields et al. |
| 2003/0092957 A1 | 5/2003 | Scott et al. |
| 2003/0095624 A1 | 5/2003 | Eberhard |
| 2003/0144570 A1 | 7/2003 | Hunter et al. |
| 2003/0153803 A1 | 8/2003 | Harmon |
| 2003/0158515 A1 | 8/2003 | Gonzalez et al. |
| 2003/0163017 A1 | 8/2003 | Tam et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0006305 A1 | 1/2004 | Hebert et al. |
| 2004/0039437 A1 | 2/2004 | Sparer et al. |
| 2004/0054366 A1 | 3/2004 | Davison et al. |
| 2004/0066884 A1 | 4/2004 | Hermann Claus et al. |
| 2004/0066904 A1 | 4/2004 | Eberhard et al. |
| 2004/0068231 A1 | 4/2004 | Blondeau |
| 2004/0087827 A1 | 5/2004 | Lubock |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0116767 A1 | 6/2004 | Lebovic et al. |
| 2004/0127765 A1 | 7/2004 | Seiler et al. |
| 2004/0147800 A1 | 7/2004 | Barber et al. |
| 2004/0171986 A1 | 9/2004 | Tremaglio, Jr. et al. |
| 2004/0215048 A1 | 10/2004 | Lubock |
| 2004/0260142 A1 | 12/2004 | Lovoi |
| 2004/0267157 A1 | 12/2004 | Miller et al. |
| 2005/0016771 A1 | 1/2005 | Mayes |
| 2005/0049521 A1 | 3/2005 | Miller et al. |
| 2005/0061533 A1 | 3/2005 | Lovoi et al. |
| 2005/0061771 A1 | 3/2005 | Murphy |
| 2005/0063509 A1 | 3/2005 | DeFreitas et al. |
| 2005/0078797 A1 | 4/2005 | Danielsson et al. |
| 2005/0080313 A1 | 4/2005 | Stewart et al. |
| 2005/0096647 A1 | 5/2005 | Steinke et al. |
| 2005/0101823 A1 | 5/2005 | Linares et al. |
| 2005/0101860 A1 | 5/2005 | Patrick et al. |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0124843 A1 | 6/2005 | Singh |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0182286 A1 | 8/2005 | Lubock |
| 2005/0226375 A1 | 10/2005 | Eberhard et al. |
| 2005/0240073 A1 | 10/2005 | Apffelstaedt et al. |
| 2005/0240074 A1 | 10/2005 | Lubock |

(56) References Cited

U.S. PATENT DOCUMENTS

| | | |
|---|---|---|
| 2005/0267320 A1 | 12/2005 | Barber et al. |
| 2005/0277577 A1 | 12/2005 | Hunter et al. |
| 2006/0014997 A1 | 1/2006 | Kindlein et al. |
| 2006/0020156 A1 | 1/2006 | Shukla |
| 2006/0020256 A1 | 1/2006 | Bell et al. |
| 2006/0030784 A1 | 2/2006 | Miller et al. |
| 2006/0074288 A1 | 4/2006 | Kelly |
| 2006/0094923 A1 | 5/2006 | Mate |
| 2006/0098855 A1 | 5/2006 | Gkanatsios |
| 2006/0100475 A1 | 5/2006 | White et al. |
| 2006/0116546 A1 | 6/2006 | Eng |
| 2006/0129062 A1 | 6/2006 | Nicoson et al. |
| 2006/0136051 A1 | 6/2006 | Furst et al. |
| 2006/0149186 A1 | 7/2006 | Wantink |
| 2006/0155209 A1 | 7/2006 | Miller et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0184192 A1 | 8/2006 | Markworth et al. |
| 2006/0199990 A1 | 9/2006 | Rioux et al. |
| 2006/0205992 A1 | 9/2006 | Lubock et al. |
| 2006/0258895 A1 | 11/2006 | Maschke |
| 2006/0291618 A1 | 12/2006 | Eberhard et al. |
| 2007/0005003 A1 | 1/2007 | Patterson et al. |
| 2007/0030949 A1 | 2/2007 | Jing et al. |
| 2007/0036265 A1 | 2/2007 | Jing et al. |
| 2007/0055144 A1 | 3/2007 | Neustadter et al. |
| 2007/0076844 A1 | 4/2007 | Defreitas et al. |
| 2007/0106108 A1 | 5/2007 | Hermann et al. |
| 2007/0142694 A1 | 6/2007 | Cutrer et al. |
| 2007/0149893 A1 | 6/2007 | Heske et al. |
| 2007/0167665 A1 | 7/2007 | Hermann et al. |
| 2007/0167666 A1 | 7/2007 | Lubock et al. |
| 2007/0191667 A1 | 8/2007 | Lubock et al. |
| 2007/0223651 A1 | 9/2007 | Wagenaar et al. |
| 2007/0225600 A1 | 9/2007 | Weibrecht |
| 2007/0242800 A1 | 10/2007 | Jing |
| 2007/0270627 A1 | 11/2007 | Cutrer et al. |
| 2008/0009659 A1 | 1/2008 | Smith et al. |
| 2008/0019581 A1 | 1/2008 | Gkanatsios |
| 2008/0045833 A1 | 2/2008 | Defreitas |
| 2008/0057298 A1 | 3/2008 | Finley |
| 2008/0064915 A1 | 3/2008 | Lubock |
| 2008/0071212 A1 | 3/2008 | Lubock et al. |
| 2008/0086083 A1 | 4/2008 | Towler |
| 2008/0091055 A1 | 4/2008 | Nguyen et al. |
| 2008/0101537 A1 | 5/2008 | Sendai |
| 2008/0112534 A1 | 5/2008 | DeFreitas et al. |
| 2008/0130979 A1 | 6/2008 | Ren |
| 2008/0177127 A1 | 7/2008 | Allan et al. |
| 2008/0188705 A1 | 8/2008 | Lubock et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0003519 A1 | 1/2009 | Defreitas |
| 2009/0010384 A1 | 1/2009 | Jing |
| 2009/0030259 A1 | 1/2009 | Quick |
| 2009/0080594 A1 | 3/2009 | Brooks |
| 2009/0080602 A1 | 3/2009 | Brooks |
| 2009/0093821 A1 | 4/2009 | Edmundson |
| 2009/0124845 A1 | 5/2009 | Lubock et al. |
| 2009/0135997 A1 | 5/2009 | Defreitas |
| 2009/0156880 A1 | 6/2009 | Allan et al. |
| 2009/0156882 A1 | 6/2009 | Chi Sing et al. |
| 2009/0171157 A1 | 7/2009 | Diederich et al. |
| 2009/0188098 A1 | 7/2009 | Acosta et al. |
| 2009/0198095 A1 | 8/2009 | Acosta et al. |
| 2009/0209805 A1 | 8/2009 | Lubock et al. |
| 2009/0213987 A1 | 8/2009 | Stein et al. |
| 2009/0268865 A1 | 10/2009 | Ren |
| 2009/0296882 A1 | 12/2009 | Gkanatsios |
| 2009/0304147 A1 | 12/2009 | Jing et al. |
| 2010/0048977 A1 | 2/2010 | Sing et al. |
| 2010/0054400 A1 | 3/2010 | Ren |
| 2010/0086188 A1 | 4/2010 | Ruth |
| 2010/0130807 A1 | 5/2010 | White et al. |
| 2010/0150306 A1 | 6/2010 | Defreitas et al. |
| 2010/0195882 A1 | 8/2010 | Ren |
| 2010/0204534 A1 | 8/2010 | Damarati |
| 2010/0226475 A1 | 9/2010 | Smith |
| 2010/0286465 A1 | 11/2010 | Benson |
| 2010/0290585 A1 | 11/2010 | Eliasson |
| 2011/0069809 A1 | 3/2011 | Defreitas et al. |
| 2012/0088952 A1 | 4/2012 | Lubock et al. |
| 2012/0178983 A1 | 7/2012 | Benson |

FOREIGN PATENT DOCUMENTS

| | | |
|---|---|---|
| DE | 3921291 | 1/1991 |
| EP | 0340881 | 10/1992 |
| EP | 0536440 A1 | 4/1993 |
| EP | 0642766 A2 | 3/1995 |
| EP | 0693293 B1 | 1/1996 |
| EP | 0719571 A2 | 7/1996 |
| EP | 775467 | 5/1997 |
| EP | 0775505 | 5/1997 |
| EP | 0853957 B1 | 7/1998 |
| EP | 0867200 A2 | 9/1998 |
| EP | 0955071 A2 | 11/1999 |
| EP | 0982001 | 3/2000 |
| EP | 1051990 A1 | 11/2000 |
| EP | 1070514 A1 | 1/2001 |
| EP | 1402922 A1 | 3/2004 |
| EP | 1428473 | 6/2004 |
| EP | 1428477 | 6/2004 |
| EP | 1541188 A1 | 6/2005 |
| EP | 1568397 | 8/2005 |
| EP | 1618924 A1 | 1/2006 |
| EP | 1759637 | 3/2007 |
| JP | 10137250 A | 5/1998 |
| JP | 2001120561 A | 5/2001 |
| RU | 2177350 C2 | 12/2001 |
| WO | WO 90/05485 | 5/1990 |
| WO | WO 92/10932 | 7/1992 |
| WO | WO 93/09724 | 5/1993 |
| WO | 9520241 A1 | 7/1995 |
| WO | 9712540 A1 | 4/1997 |
| WO | WO 97/19723 | 6/1997 |
| WO | 9745053 A2 | 12/1997 |
| WO | 9815315 A1 | 4/1998 |
| WO | WO 98/16903 | 4/1998 |
| WO | WO 99/11325 | 3/1999 |
| WO | 9934869 A1 | 7/1999 |
| WO | WO 99/33515 | 7/1999 |
| WO | WO 99/42163 | 8/1999 |
| WO | WO 00/51484 | 9/2000 |
| WO | 0059378 | 10/2000 |
| WO | 0114011 A1 | 3/2001 |
| WO | 0143826 A1 | 6/2001 |
| WO | 0158346 A1 | 8/2001 |
| WO | 0195808 | 12/2001 |
| WO | 0209599 A2 | 2/2002 |
| WO | 02069862 A1 | 9/2002 |
| WO | WO 03/020114 | 3/2003 |
| WO | 03079907 | 10/2003 |
| WO | 2004043531 A2 | 5/2004 |
| WO | WO 2004/043535 | 5/2004 |
| WO | 2005037363 | 4/2005 |
| WO | 2005037363 A2 | 4/2005 |
| WO | 2005039655 A1 | 5/2005 |
| WO | 2005039665 A1 | 5/2005 |
| WO | WO 2005/051197 | 6/2005 |
| WO | 2005067442 A2 | 7/2005 |
| WO | WO 2005110230 | 11/2005 |
| WO | WO 2005112767 | 12/2005 |
| WO | WO 2006/055830 | 5/2006 |
| WO | WO 2006/058160 | 6/2006 |
| WO | 2007027831 A1 | 3/2007 |

(56) References Cited

FOREIGN PATENT DOCUMENTS

| WO | 2007143560 A2 | 12/2007 |
| WO | WO 2008/067557 | 6/2008 |
| WO | WO 2009/079170 | 6/2009 |

OTHER PUBLICATIONS

Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45(1).

International Search Report for PCT/US2008/003364 mailed Aug. 27, 2008.

Written Opinion of the International Searching Authority for PCT/US2008/003364 dated Sep. 15, 2009.

International Preliminary Report on Patentability for PCT/US2008/003364 issued Aug. 3, 2010.

International Search Report for PCT/US2008/003217 mailed Aug. 12, 2008.

Written Opinion of the International Searching Authority for PCT/US2008/003217 dated Sep. 12, 2009.

International Preliminary Report on Patentability for PCT/US2008/003217 dated Mar. 21, 2011.

International Search Report for PCT/U803/33775 mailed Jun. 21, 2004.

International Preliminary Report on Patentability for PCT/US03/33775 dated Oct. 10, 2007.

International Search Report for PCT/US2006/044067 mailed Dec. 18, 2007.

Written Opinion of the International Searching Authority for PCT/US2006/044067 dated Jan. 11, 2009.

International Preliminary Report on Patentability for PCT/US2006/044067 dated Oct. 2, 2009.

International Search Report for PCT/US2006/043891 mailed Sep. 25, 2007.

Written Opinion of the International Searching Authority for PCT/US2006/043891 dated May 18, 2008.

International Preliminary Report on Patentability for PCT/US2006/043891 dated Jan. 12, 2009.

Office Action dated Feb. 1, 2013 in U.S. Appl. No. 13/571,495.

Office Action dated Mar. 13, 2013 in U.S. Appl. No. 13/649,668.

*SenoRX, Inc. v. Hologic, Inc.;* District Court for the District of Delaware, Case No. 1:12-cv-00173-LPS-CJB, Complaint filed Feb. 10, 2012.

*SenoRX, Inc. v. Hologic, Inc.;* District Court for the District of Delaware, Case No. 1:12-cv-00173-LPS-CJB, Hologic, Inc.'s Answer to Complaint and Counterclaim filed on May 23, 2012.

*SenoRX, Inc. v. Hologic, Inc.;* District Court for the District of Delaware, Case No. 1:12-cv-00173-LPS-CJB, SenoRX's Answer to Counterclaim filed on Jun. 18, 2012.

*SenoRX, Inc. v. Hologic, Inc.;* District Court for the District of Delaware, Case No. 1:12-cv-00173-LPS-CJB, Joint Claim Construction Chart, filed Nov. 16, 2012.

Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.

Stubbs, J. B., et al., "Preclinical Evaluation of a Novel Device for Delivering Brachytherapy to the Margins of Resected Brain Tumor Cavities", J. Neurosurg 96, Feb. 2002, pp. 335-343, vol. 96.

Das, R. K., of al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.

Complete file history for U.S. Appl. No. 11/266,994.
Complete file history for U.S. Appl. No. 12/493,884.
Complete file history for U.S. Appl. No. 12/692,289.

Partial file history for U.S. Appl. No. 12/710,308 from Aug. 1, 2013 to present.
Complete file history for U.S. Appl. No. 12/775,636.
Complete file history for U.S. Appl. No. 11/682,681.
Complete file history for U.S. Appl. No. 11/688,033.
Complete file history for U.S. Appl. No. 12/694,741.
Complete file history for U.S. Appl. No. 13/299,376.

Paul V. Harper, "Some Therapeutic Applications of Radioisotopes", Journal of the Mississippi State Medical Association, Oct. 1966, vol. VII, pp. 526-533.

"Variable shield for radiation-therapy source wire and centering catheter", Research disclosure, Mason Publications, Hampshire, GB, vol. 438, No. 48, Oct. 2000, XP007126916.

Gregory K. Edmundson, et al., "Dosimetric Characteristics of the Mammosite RTS, a New Breast Brachytherapy Applicator", Int. J. Radiation Oncology Biol. Phys, vol. 52, No. 4, pp. 1132-1139, 2002.

Melvin A. Astrahan, PhD et al., "Optimization of Mammosite therapy", Int. J. Radiation Oncology Biol. Phys, vol. 58, No. 1, pp. 220-232, 2004.

Philip H. Gutin, et al., "A coaxial catheter system for afterloading radioactive sources for the interstitial irradiation of brain tumors", J. Neurosur, vol. 56, pp. 734-735, 1982.

R.D. Ashpole et al., "A New Technique of Brachytherapy for Malignant Gliomas with Caesium-137; A New Method Utilizing a Remote Afterloading system", Clinical Oncology, (1990).

Abstracts of the 11th International Conference on Brain tumor Research and Therapy Oct. 31-Nov. 3, 1995, Silverado Country Club and Resort, Napa, California, Journal of Neuro-Oncology 28:72, 1996.

Johannesen, T.B. et al, "Intracavity Fractioned Balloon Brachytherapy in Glioblastoma", Acta Neurochir (Wien) (1999) 141: 127-133.

Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.

Partial file history for U.S. Appl. No. 12/493,884 from Jan. 7, 2014 to present.

Partial file history for U.S. Appl. No. 12/694,741 from Jan. 14, 2014 to present.

Cuttino, L. W., et al., "CT-Guided Multi-Catheter Insertion Technique for Partial Breast Brachytherapy: Reliable Target Coverage and Dose Homogeneity", Brachytherapy 4, 2005, pp. 10-17, Elsevier.

Glasgow, G. P., et al. "Remote Afterloading Technology", AAPM Report No. 41, 1993, pp. i-vi and 1-107, American Institute of Physics, Inc.

Hoshino, T., "Brain Tumor Research Center", Abstracts of the 11th Conference on Brain Tumor Research and Therapy, Journal of Neuro-Oncology 28, 1996, pp. 31-113.

Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.

Devic, et al., "Advantages of Inflatable Multichannel Endorectal Applicator in the Neo-Adjuvant Treatment of Patients With Locally Advanced Rectal Cancer With HDR Brachytherapy", Journal of Applied Clinical Medical Physics, Spring 2005, pp. 44-49, vol. 6, No. 2.

Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.

Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.

Walton, R. J., "Therapeutic Uses of Radioactive Isotopes in the Royal Cancer Hospital", The British Journal of Radiology, 1950, pp. 559-599, William Heinemann, Publisher.

(56) References Cited

OTHER PUBLICATIONS

Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.
Low-Beer, B. V. A., "The Therapeutic Use of Radioactive Isotopes", "Practical Therapeutics", Dec. 1954, pp. 69-87, vol. X, No. 6.
Muller, J. H., "Radiotherapy of Bladder Cancer by Means of Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J. B. Lippincott Company, Philidelphia.
Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.
Hewitt, C. B., et al., "Update on Intracavitary Radiation in the Treatment of Bladder Tumors", The Journal of Urology; Official Journal of the American Urological Association, Inc., 1981, pp. 323-325, vol. 126 September, The Williams & Wilkins Co.
Hieshima,G. B., et al. "A Detachable Balloon for Therapeutic Transcatheter Occlusions 1", Technical Notes, Jan. 1981, pp. 227-228, vol. 138.
Russel, A. H., et al, "Intracavitary Irradiation for Carcinoma of the Urinary Bladder: Rationale, Technique, and Preliminary Results", Int. J. Radiation Oncology. Phys,. 1984, pp. 215-219, vol. 10, Pergamon Press Ltd.
Yin, W., "Brachtherapy of Carcinoma of the Esophagus in China, 1970-1974 and 1982-1984", Brachytherapy HDR and LDR, May 4-6, 1989, pp. 52-56.
Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press plc.
Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.
Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.
Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.
Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.
Micheletti, E., et al., "High-Dose-Rate Brachytherapy for Poor-Prognosis, High-Grade Glioma: (Phase II) Preliminary Results", Turned, 1996, pp. 339-344.
Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.
Nag, S., et al., "Remote Controlled High Dose Rate Brachytherapy", Critical Reviews in Oncology/Hematology 22, 1996, pp. 127-150, Elsevier Science Ireland Ltd.
Sylvester, J., et al., "Interstitial Implantation Techniques in Prostate Cancer" Journal of Surgical Oncology 1997; 66: 65-75, Wiley-Liss, Inc.
Tan, L. T., et al., Radical Radiotherapy for Carcinoma of the Uterine Cervix Using External Beam Radiotherapy and a Single Line Source Brachytherapy Technique: The Clatterbridge Technique, The British Journal of Radiology, 70, date Dec. 1997, pp. 1252-1258.
Kuettel, M. R., et al., "Treatment of Female Urethral Carcinoma in Medically Inoperable Patients Using External Beam Irradiation and High Dose Rate Intracavitary Brachytherapy" The Journal of Urology, May 1997, pp. 1669-1671, vol. 157, The American Urological Association, Inc.
Slevin, N. J., et al., "Intracavitary Radiotherapy Boosting for Nasopharynx Cancer" The British Journal of Radiology, 70, Apr. 1997, pp. 412-414.
Sneed, P, K., et al., Interstitial Brachytherapy Procedures for Brain Tumors, Seminars in Surgical Oncology 1997; 13: 157-166, Wiley-Llss, Inc.
Dempsey, J. F., et al., "Dosimetric Properties of a Novel Brachytherapy Balloon Applicator for the Treatment of Malignant Brain-Tumor Resection-Cavity Margins" Int. J. Radiation Oncology Biol. Phys., May 1998, pp. 421-429, vol. 42, No. 2, Elsevier.
Kolotas, C., et al., "CT Guided Interstitial High Dose Rate Brachytherapy for Recurrent Malignant Gliomas", The British Journal of Radiology, 72, (1999), pp. 805-808.
Demanes, D, J., et al., "The Use and Advantages of a Multichannel Vaginal Cylinder in High-Dose-Rate Brachytherapy", Int. J. Radiation Oncology Biol. Phys., (1999), pp. 211-219, vol. 44, No. 1, Elsevier Science Inc.
Debicki, M. P., et al., "Localized Current Field Hyperthermia in Carcinoma of the Cervix: 3-D Computer Simulation of SAR Distribution", International Journal of Hyperthermia, 1999, pp. 427-440, vol. 15, No. 5.
Garipagaoglu, M, et al., "Geometric and Dosimetric Variations of ICRU Bladder and Rectum Reference Points in Vaginal Cuff Brachytherapy Using Ovoids", Int. J. Radiation Oncology Biol. Phys.. 2004, pp. 1607-1615, Elsevier Inc.
Bowsher, W. G., et al., "Update on Urology-Prostate Cancer, 4-Treatment of Local Disease", European Journal of Surgical Oncology, 1995 pp. 679-682, vol. 21, No. 6.
Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.
Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.
Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, 50/3/MAR.
Hine, G. J., et al., "Isodose Measurements of Linear Radium Sources in Air and Water by Means of an Automatic Isodose Recorder",The American Journal of Roentgenology and Radium Therapy, 1950, pp. 989-998, vol. 64, No. 6, The Societies.
Walton, R. J., et al., Radioactive Solution (24Na and 82 Br) in the Treatment of Carcinoma of the Bladder:, British Medical Bulletin, 1952, pp. 158-165, Medical Dept., The British Council.
Marshall V. F., et al., "Current Clinical Problems Regarding Bladder Tumors", Symposium on Bladder Tumors, 1956, pp. 543-550, 9/3/May-Jun, J. B. Lippincott Co, Etc.
Hewitt, C. B., et al., "Intracavitary Radiation in the Treatment of Bladder Tumors", The Journal of Urology, vol. 107, Apr. 1972, pp. 603-606, The Williams & Wilkins Co.
Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.
Nag, S., et al., "The Future of High Dose Rate Brachytherapy", High Dose Rate Brachytherapy: A Textbook, 1994, pp. 447-453, Future Publishing Company, Inc. , Armonk, New York 10504.
Wang, C. C., "Carcinoma of the Nasopharynx", Radiation Therapy of Head and Neck Neoplasms, 1997, pp. 257-280, Chapter 10, Wiley-Liss, Inc.
Gaspar, L. E., et al., "Esophageal Brachytherapy", Principles and Practice of Brachytherapy, 1997, pp. 305-321, Futrua Publishing Company, Inc., Armouk, New York.
Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.

(56) References Cited

OTHER PUBLICATIONS

Akagi, Y, et al., "Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.

"Essentials for life: Senographe Essential Full-Field Digital Mammography system", GE Health-care Brochure, MM-0132-05.06-EN-US, 2006, 12 pgs.

"Filtered Back Projection," (NYGREN) published May 8, 2007; URL:http://web.archive.org/web/19991010131715/http://www.owlnet.rice.edu/-.about.e1ec539/Projects97/cult/node2.html, 2 pgs.

Kita et al., "Corresponding between different view breast X-rays using simulation of breast deformation", Proceedings 1998 IEE ComputerSociety Conference on Computer Vision and Pattern Recognition, Santa Barbara, CA, Jun. 23-25, 1998, pp. 700-707.

Smith, A., "Fundamentals of Breast Tomosynthesis", White Paper, Hologic Inc. WP-00007, Jun. 2008.

Wheeler F. W., et al. "Micro-Calcification Detection in Digital Tomosynthesis Mammography" Proceedings of SPIE, Dec. 11, 2001 to Dec. 15, 2001, vol. 6144, Feb. 13, 2006.

Wu Tao, et al. "Tomographic Mamography Using a Limited Number of Low-Dose Cone-Beam Projections Images" Medical Physics, vol. 30, No. 3, Mar. 1, 2003, pp. 365-380.

\* cited by examiner

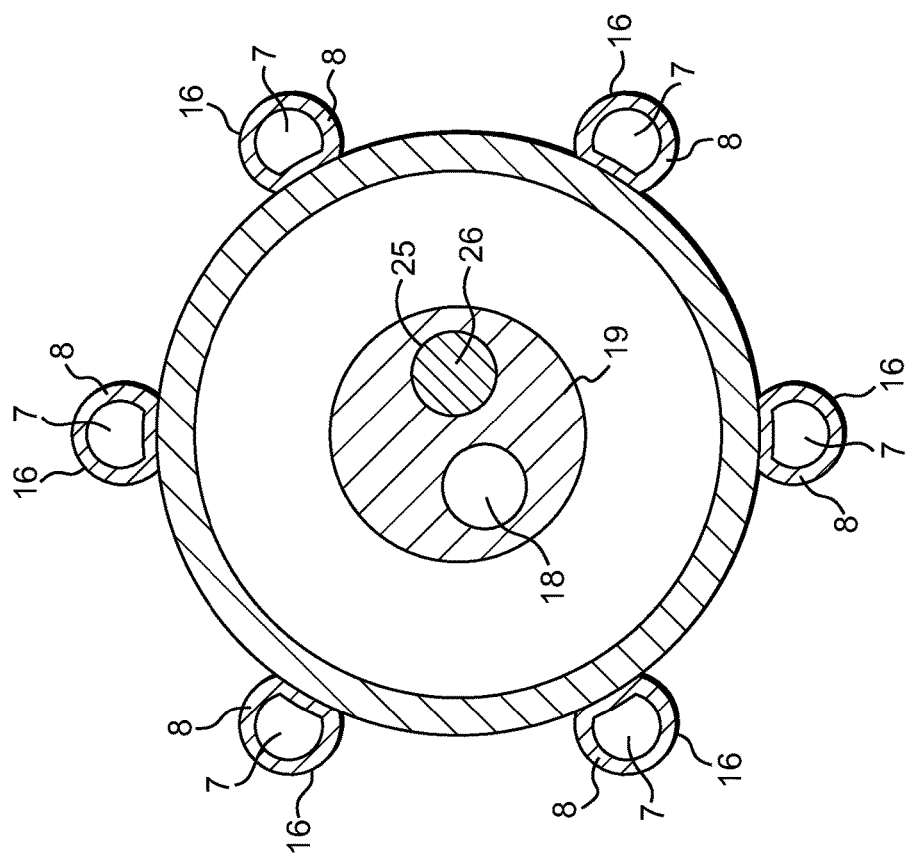
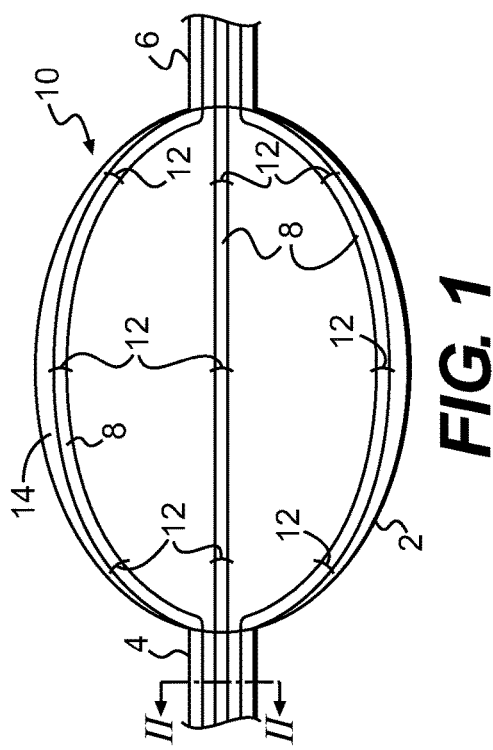

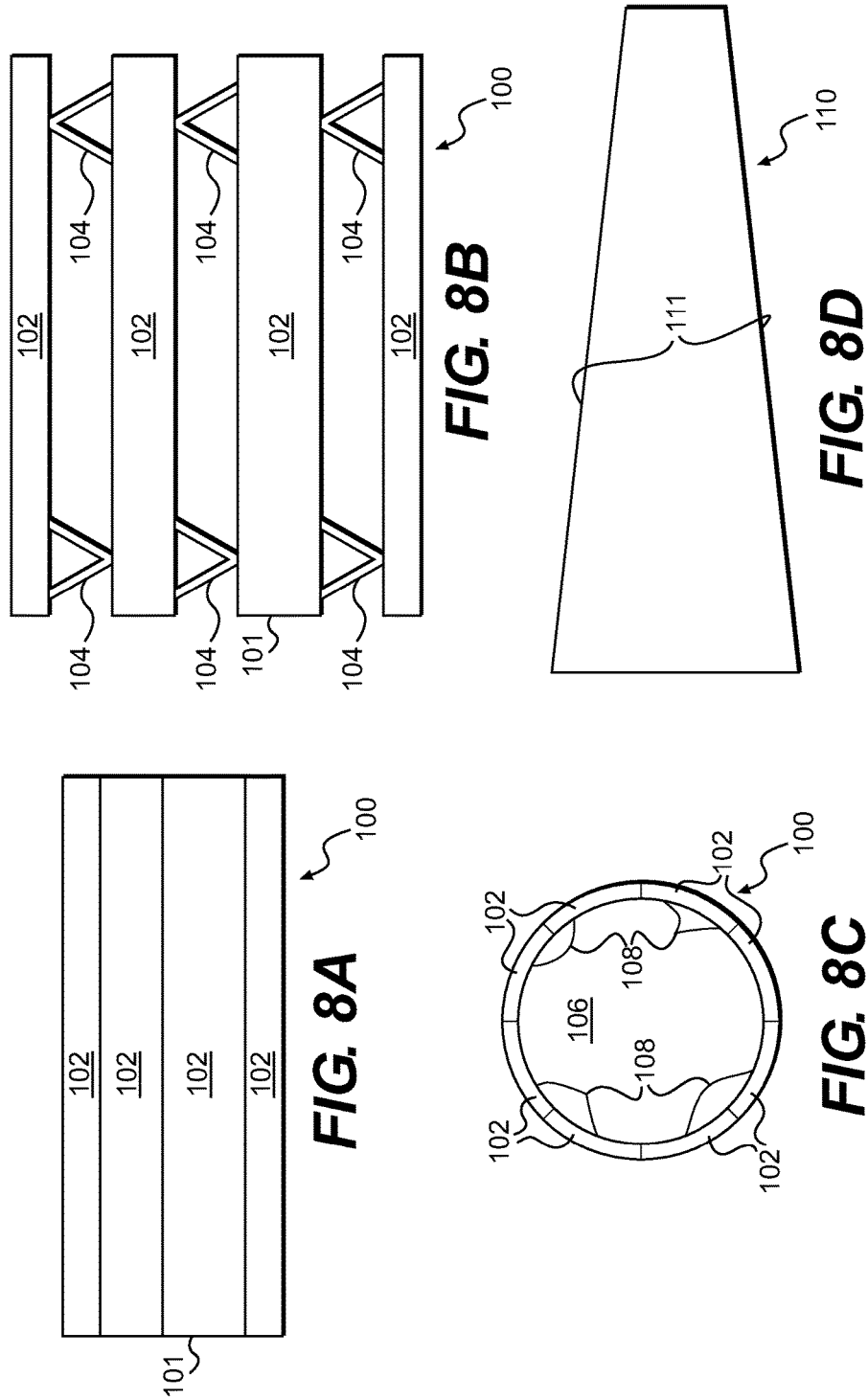

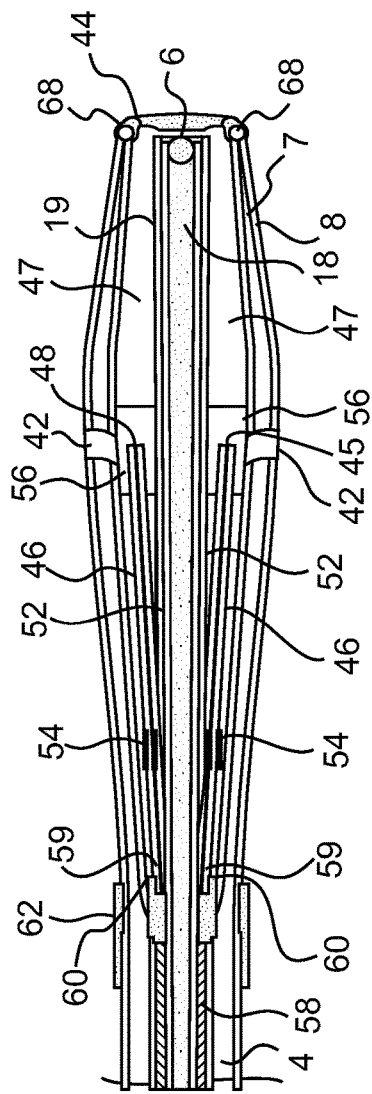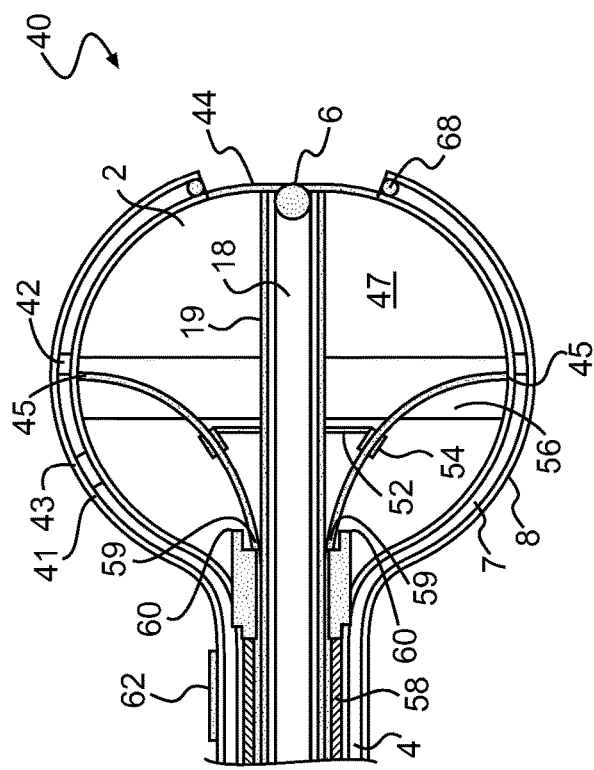
FIG. 10A
FIG. 10B

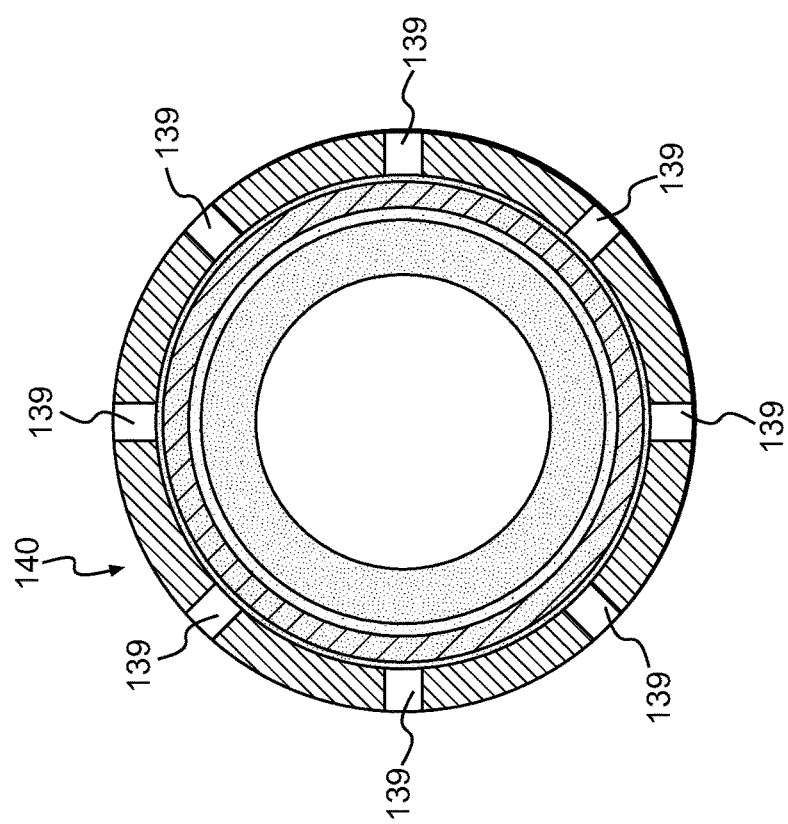
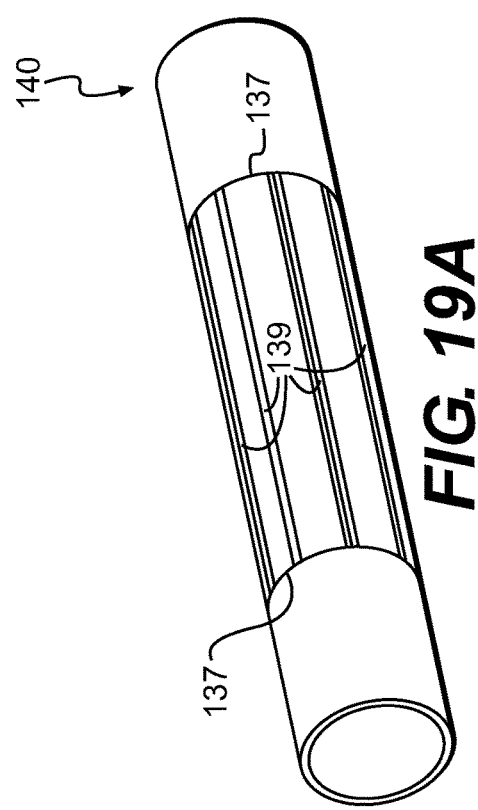

EXPANDABLE BRACHYTHERAPY DEVICE

CROSS-REFERENCE TO RELATED APPLICATIONS

This application is a continuation of U.S. patent application Ser. No. 12/775,636, filed on May 7, 2010, which is a continuation of U.S. patent application Ser. No. 12/493,884, filed on Jun. 29, 2009, which is a continuation of U.S. patent application Ser. No. 11/266,994, filed on Nov. 4, 2005, now U.S. Pat. No. 7,662,082, issued Feb. 16, 2010, which is a non-provisional of U.S. provisional application No. 60/625,355, filed on Nov. 5, 2004, pursuant to 35 U.S.C. §119(e), the texts of which are hereby incorporated by reference in their entirety.

BACKGROUND OF THE INVENTION

1. Field of the Invention

The invention relates to the field of brachytherapy. In particular the invention relates to an expandable brachytherapy device and methods of using it with the ability to provide a tailored radioactive dose profile.

2. Description of the Related Technology

A variety of devices exist for performing brachytherapy on the body. Exemplary devices that are employed in body cavities or cavities created in the body by surgery include, for example, brachytherapy devices for treatment of breast cancer, uterine cancer, prostate cancer, treatment of a cavity left by removal of a tumor, cyst, polyp or similar mass, and treatment or prevention of restenosis. Some of these devices are merely implants that are implanted in a cavity in the body to deliver the treatment. However, certain types of devices are expandable to allow insertion of the device into the body in an unexpanded state, and subsequent expansion of the device to deliver the brachytherapy. Such expandable devices are particularly useful for the treatment of, for example, breast cancer, vascular restenosis and uterine cancer.

Breast cancer affects many women. Not only is breast cancer a serious and life threatening illness, quite frequently the methods involved in treating breast cancer can have dramatic life altering cosmetic ramifications for a woman. Treatments, such as mastectomies, involve radical surgical procedures that while saving a patient's life, oftentimes extract a high price on both the physical and mental health of a patient. Other treatment methods may be preferable because of these drawbacks.

One method of treating breast cancer is by subjecting a cancerous tumor to radiation treatment. Although, doing this can be as effective in curing breast cancer as more radical procedures, there is a chance that the intense radiation used in destroying the cancer can adversely affect healthy tissue in the area surrounding the area treated. One method for avoiding potential damage to healthy tissue is through the use of special brachytherapy treatment procedures. Applying radiation treatment according to a specialized treatment plan may permit a more effective treatment while minimizing undesirable consequences of that treatment.

In a patient with breast cancer one method of treating the cancer is to excise the tumor without removal of the entire breast. Excising the tumor is performed in a procedure called a lumpectomy. A lumpectomy is the surgical removal of a tumor in the breast, along with a small margin of surrounding normal breast tissue. A lumpectomy may also be called a wide excision biopsy, breast conserving therapy or quadrantectomy (this latter term is used when up to one fourth of the breast is removed). The procedure is often performed on women with small or localized breast cancers and can be an attractive surgical treatment option for breast cancer because it allows women to maintain most of their breast after surgery. Several studies have shown that women with small breast tumors have an equal chance of surviving breast cancer regardless of whether they have a lumpectomy, followed by a full course of radiation therapy, or mastectomy (complete breast removal, which generally does not require post-operative radiation treatment). A lumpectomy may be performed using a local anesthetic, sedation, or general anesthesia, depending on the extent of the surgery needed. The surgeon makes a small incision over or near the breast tumor and excises the lump or abnormality along with a margin of an appropriate thickness of normal surrounding breast tissue.

Upon excision of the tumor, a cavity is created in the space where the tumor once existed, however some cancerous tissue may remain at the margins. In order to ensure a full recovery, radiation therapy is applied in the area where the tumor was located. An exemplary method for performing radiation therapy is to employ an expandable brachytherapy device that has been inserted into the cavity that remains after the lumpectomy.

One method for using brachytherapy to treat breast cancer involves placing a radioactive source within a balloon catheter that has been inserted into the cavity formed by the lumpectomy. The radioactive source is placed within the central lumen of the balloon catheter, which is generally centered on the longitudinal axis of the expanded device. This practice places significant limitations on the ability to customize the treatment for a particular patient. For example, placing the radioactive source within the central lumen of the balloon does not permit the radioactive dosage to be tailored to treat primarily only the areas surrounding the cavity that require irradiation. Also, placement of the radioactive source in the central lumen may result in healthy tissue being exposed to undesirable amounts of radiation during exposure of the tissue requiring treatment and/or underexposure of tissue that is a high risk for cancer recurrence. This is at least partially due to the fact that the cavity created by the lumpectomy is generally non-uniform in shape, thereby creating a situation where the distance from the central lumen to tissue at the edge of the cavity may vary at different locations in the cavity, or healthy tissue is located in the treatment region of the radiation field. This is also partially due to the fact that healthy tissue may be located closer to the central lumen at some locations than at other locations. This means that in the interest of preserving healthy tissue and minimizing dose to the skin, the physician may have to use a dose distribution that is less effective than desired. Alternatively, should the physician employ a dose sufficient to ensure effective treatment, healthy tissue may be damaged. As a result, many physicians opt for alternative treatments to avoid the risks associated with the prior art devices.

The catheter material must be stiff enough to maintain structural and functional integrity and flexible enough to minimize discomfort and the chance of injury. A broad range of technical properties (modulus of elasticity, apparent flexural modulus, and durometer) can be achieved by using variations on the thousands of different resins that are current commercially available. The catheters are typically constructed of many different materials such as: polyvinyl chloride (PVC), polyethylene (PE), polyolefin copolymer (POC), nitinol, fluoropolymers, polyurethane (PU), polyetheretherketone (PEEK), polyimide, polyethylene terephthalate (PET), super-elastics, and shape memory materials. The materials used may also be rendered radio-opaque by the loading of additives such as barium sulfate.

Some prior art brachytherapy methods using balloon catheters to deliver the radioactive source are discussed below.

An article by Paul V. Harper from 1966, entitled "Some Therapeutic Applications of Radioisotopes," published in the Journal MSMA, discusses use of balloon catheters for the treatment of cancer. Harper describes a water filled balloon provided with a central glass tube which can be used to fill the balloon. A radioactive tantalum wire is inserted into the central glass tube once the balloon is located at the treatment area and inflated in order to provide brachytherapy to the treatment area. The Harper device provides an isodose curve that is substantially the same shape as the inflated balloon surface of the device. Harper also describes filling a specially-designed catheter with a liquid solution of radio-isotope after the catheter has been inserted into the body in order to provide radiation to the treatment area. In addition, Harper describes the provision of plastic spheroids coated with a radioactive material, which may be packed into a cavity in the body for delivery of a brachytherapy treatment.

Another method for interstitial brachytherapy involves the insertion of a plurality of hollow needles or catheters into the breast and through the surgical cavity in the breast, followed by placement of radioactive sources in the needles according to a predetermined treatment plan. High dose rate iridium sources as well as seed strands are examples of the type of radiation sources that may be employed in this type of interstitial brachytherapy.

U.S. Pat. No. 6,482,142 to Winkler et al. discloses a catheter for use in a method for interstitial brachytherapy in a tumor bed. Winkler discloses a device, shown in FIG. 4, having a radiation source 82 made of three wires 84, 86, and 88, each having a plurality of radiation particles. Wire 86 is a straight wire that extends along the axis of the device and wires 84 and 88 are curved wires that may be made from a shape memory material to allow deformation of the wires for insertion and removal from the catheter. More or fewer wires can be provided.

U.S. Pat. No. 5,302,168 to Hess discloses using a balloon catheter for the treatment of restenosis. FIGS. 2-4 show a balloon 36 with radioactive elements 38 attached to the outer surface thereof. Alternatively, the surface of the balloon may be coated with radioactive material. It appears from FIG. 4, that the radioactive elements 38 expand from a first size, shown in FIG. 2, to a second, larger size, shown in FIG. 4, as the balloon 36 expands.

U.S. Pat. No. 5,863,284 to Klein discloses a balloon catheter for use in angioplasty. Radioactive sources 30 are spaced around the circumference of the balloon. The sources may be attached to the balloon (FIGS. 4 and 4a) or may be contained in a sleeve 48 designed to fit over the balloon (FIGS. 9-10). At col. 13, lines 1-30, a distal portion 18 includes a plurality of slits to allow expansion of distal portion 18 when the balloon is inflated to thereby position radioactive elements 30 at substantially uniform intervals around the inflated balloon. At col. 14, lines 46+, a device is described wherein the distal portion 18 includes an elastomeric expansible region 38 which allows expansion of the distal portion 18 when the balloon is expanded to maintain equal spacing of the radioactive elements about the circumference of the balloon. In the embodiment of FIGS. 7-8 described at col. 15, lines 5-19, the distal portion 18 includes a plurality of folds which allow expansion of the distal portion when the balloon is inflated. At col. 15, lines 20-25, the embodiment shown in FIGS. 9-10 is described. In this embodiment, a sleeve 48 containing a plurality of folds is fitted over the balloon. The sleeve 48 is expandable by virtue of the folds when the balloon is expanded. In yet another embodiment, the radioactive element is integrally formed with the balloon such that the radioactive element moves with the balloon as the balloon is expanded. To improve the uniformity of the radiation dose, the device may employ a secondary radiation source in the form of a guide wire inserted into the central lumen of the balloon catheter.

The devices discussed above offer various methods for using a balloon catheter in brachytherapy, but do not address the provision of customized dosing which can be achieved through the use of certain advantageous features of the present invention discussed below and set out in detail in the detailed description of the preferred embodiments. It is an object of certain embodiments of the invention to provide an apparatus and method for providing tailored brachytherapy treatment.

SUMMARY OF THE INVENTION

In a first aspect, the present invention relates to a brachytherapy device. The device includes a movable surface portion. One or more source lumens are situated outside the surface portion of the device and extend a distance sufficient to permit a radiation source to be loaded into the one or more source lumens from outside the body after the device is positioned inside a body or surgical cavity for therapy. One or more sources of radiation may be placed within one or more of the source lumens to provide a customized radiation dose to a treatment area. One advantage of the present invention is that the sources of radiation may be placed at different locations along the length of each source lumen for the same or different time periods to allow for customization of the dose delivered to the treatment area.

In a second aspect, the present invention relates to a method of providing brachytherapy. The method involves the step of inserting a brachytherapy device into a body or surgical cavity. The brachytherapy device has one or more source lumens located outside a movable surface portion of the device. The method further includes the steps of moving the surface portion within the cavity and placing one or more radioactive sources within at least one of the source lumens to provide a customized radiation dose to a treatment area.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 1 shows a side view of an expanded device in accordance with a first embodiment of the present invention.

FIG. 2 shows a cross-sectional view of the proximal portion of the expanded device taken along line II-II of FIG. 1.

FIG. 8A shows a side view of a cylinder in the unexpanded stated formed by a plurality surface portions hingedly attached to one another.

FIG. 8B shows the same side view of the cylinder of FIG. 8A in the expanded state.

FIG. 8C shows a view of the proximal end of the cylinder of FIGS. 8A-8B.

FIG. 8D shows a conical expander for use in expansion of the device of FIGS. 8A-8C.

FIGS. 10A-10B show longitudinal cross-sectional views of one embodiment of the expandable device shown in FIG. 9 employing flexible rods to expand the expandable surface portion, with FIG. 10A showing the device in the unexpanded state and FIG. 10B showing the device in the expanded state.

FIG. 19A shows an alternative embodiment of a mechanism for expanding a device.

FIG. 19B shows a cross sectional view of the mechanism shown in FIG. 19A

DETAILED DESCRIPTION OF THE PREFERRED EMBODIMENT(S)

Figure 3:
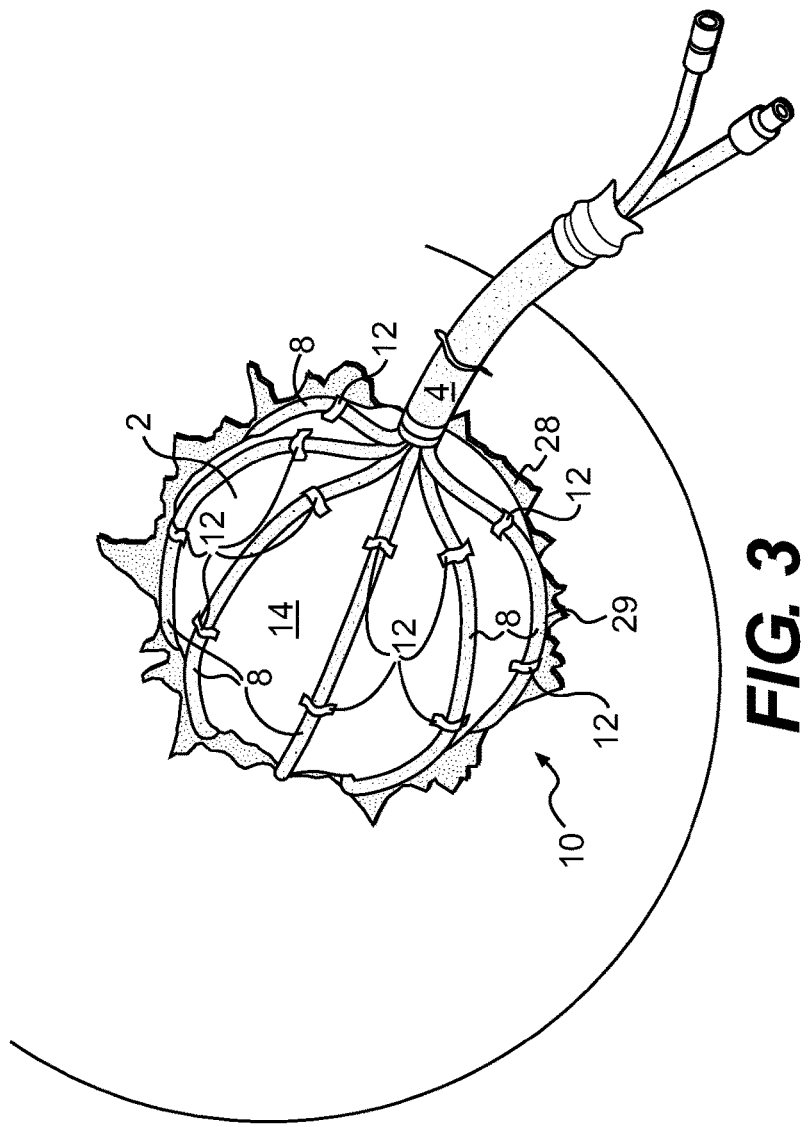
FIG. 3 shows the balloon catheter of FIGS. 1-2 located in a cavity of a patient.

Referring now to the drawings, wherein like reference numerals designate corresponding structure throughout the several views, and referring to FIG. 1, a side view of a first embodiment of the present invention is shown. In this first embodiment of the invention, a brachytherapy device is provided with an internal lumen and includes a surface portion that is movable. One or more source lumens are situated outside the movable surface portion of the device and extend a distance sufficient to permit a radiation source to be loaded into the one or more source lumens from outside the body after the device is positioned in an existing body cavity or surgical cavity created by a surgical procedure for therapy. Thus, the devices of the present invention are applicable to both interstitial and inter-cavital brachytherapy procedures. One or more sources of radiation may be placed within one or more of the internal and source lumens to provide a customized radiation dose to a treatment area.

In the first embodiment of the invention shown in FIG. 1, the brachytherapy device is a balloon catheter 10 that includes a movable surface portion 2 formed by the surface of a balloon 14. As shown in FIG. 1, balloon 14 of balloon catheter 10 is in the inflated state. Balloon catheter 10 has a proximal portion 4, and a distal portion 6. Proximal portion 4 is of sufficient length to extend from balloon 14 to a location outside the body when balloon 14 is positioned within a surgical or body cavity. Distal portion 6 provides a location for securing tubes 8, which define external source lumens 7, to balloon catheter 10. Tubes 8 may be secured to proximal and distal portions 4, 6 of balloon catheter 10 by any suitable means such as an adhesive, melt bonding, staples, clips, or other conventional securing mechanisms. Tubes 8 may also be formed integrally with one or both of proximal and distal portions 4, 6 of balloon catheter 10. In yet another embodiment, Tubes 8 are slidably secured to one or both of proximal and distal portions 10 within a manifold 30, such as that shown in FIG. 7, which forms part of one or both of proximal and distal portions 4, 6. In this manner, slack in tubes 8 may be taken up by sliding movement of a portion of tubes 8 through manifold 30 as the movable surface portion 2 moves. Manifold 30 may be provided at either the proximal portion 4 or distal portion 6 of the device.

As shown in FIGS. 1-2, balloon catheter 10 is provided with a plurality of external source lumens 7 defined by tubes 8 which are attached to the proximal and distal portions 4, 6 of balloon catheter 10, by a suitable attachment means. Tubes 8 may have any cross-sectional shape, such as, for example, round, oval, elliptical, square, rectangular, triangular, pentagonal, hexagonal, ribbed, etc. Preferred tubes 8 are round, oval or elliptical to avoid any corners or edges that might catch during insertion or retraction of the brachytherapy device into or out of the body or surgical cavity, but may also employ strengthening ribs with rounded edges, if desired. Source lumens 7 may also have any cross-sectional shape, including at least round, oval, elliptical, square, rectangular, triangular, pentagonal, hexagonal, etc. Source lumens 7 are provided for the purpose of receiving one or more radiation sources for treatment of the patient. The brachytherapy device may include any number of external source lumens 7, and may include, for example, 1-source lumens 7, 2-14 20 source lumens 7, or, optionally, 4-16 source lumens 7. Different treatment circumstances may dictate the use of different numbers of source lumens 7 depending on, for example, the size of the surgical or body cavity, and the treatment plan. One or more radiation sources may be inserted into each of source lumens 7 to provide a customized treatment as described in greater detail below. In order to provide a predictable customized treatment, it is desirable to ensure that tubes 8 are positioned in predetermined locations relative to a reference location, such as the longitudinal axis of balloon catheter 10, so that dose calculations are based on an accurate representation of the location of source lumens 7 and hence the radiation sources inserted into source lumens 7.

In the embodiment of FIG. 1, tubes 8 are not attached to movable surface portion 2 of balloon 14, which allows tubes 8 to move relative to movable surface portion 2 of balloon 14. This is a useful feature of this embodiment since it allows tubes 8 to conform to the shape of movable surface portion 2, when it is expanded, without substantial deformation of source lumens 7 as a result of inflation of balloon 14. Tubes 8 may be secured to movable surface portion 2 by a suitable securing means such as tack bonding or using a loop 12. Loops 12 may be attached at any location on movable surface portion 2. As shown, loops 12 are attached midway between proximal portion 4 and distal portion 6. Loops 12 are attached to movable surface portion 2 and each loop 12 surrounds a tube 8 to retain tube 8 in close proximity to movable surface portion 2 in the area of loop 12. Loops 12 are shown with a minimal length but loops 12 may also extend some length in the axial direction. Contact between loop 12 and tube surface 16 of tube 8 restricts the movement of tube 8 in a radial direction relative to movable surface portion 2. Loops 12 may be attached to movable surface portion 2 by any suitable, conventional securing means. Loops 12 may be made of either a rigid material or a flexible material, though loops 12, in the embodiment shown, are made from a semi-rigid or flexible material that is biocompatible since loops 12 will contact body tissue during use of the device.

By securing tubes 8 via loops 12 to movable surface portion 2, tubes 8 are free to move in the axial direction relative to movable surface portion 2, which allows slack in tubes 8 to be taken up during inflation of balloon 14, thereby preventing substantial deformation of source lumens 7 as a result of movement of movable surface portion 2. The longitudinal axis of balloon catheter 10 runs from the center of proximal portion 4 to the center of distal portion 6. Slack in tubes 8 may be provided in a number of different ways. For example, the length of tubes 8 that extends from proximal portion 4 to distal portion 6 may be selected to provide slack in that portion of tubes 8. In that embodiment, tubes 8 are slidably secured at the proximal portion 4 and have sufficient length between proximal portion 4 and distal portion 6 to conform to the movable surface portion 2 when balloon 14 is in the inflated condition. In an alternative embodiment, instead of attaching tubes 8 to proximal portion 4, tubes 8 can be attached to a movable attachment location, which is associated with, or forms part of, proximal portion 4. In this manner, slack in tubes 8 can be provided outside the body or surgical cavity instead of between proximal portion 4 and distal portion 6, thereby resulting in a potential reduction in the diameter of balloon catheter 10 that has to pass through the incision to be inserted into the body. In this embodiment, the movable attachment location may be located at the proximal portion 4 for sliding movement in a direction substantially parallel to the longitudinal axis of the device. The slack can also be provided at the distal portion 6 of the device by providing the movable attachment portion at the distal portion 6 of the device.

Figure 7:
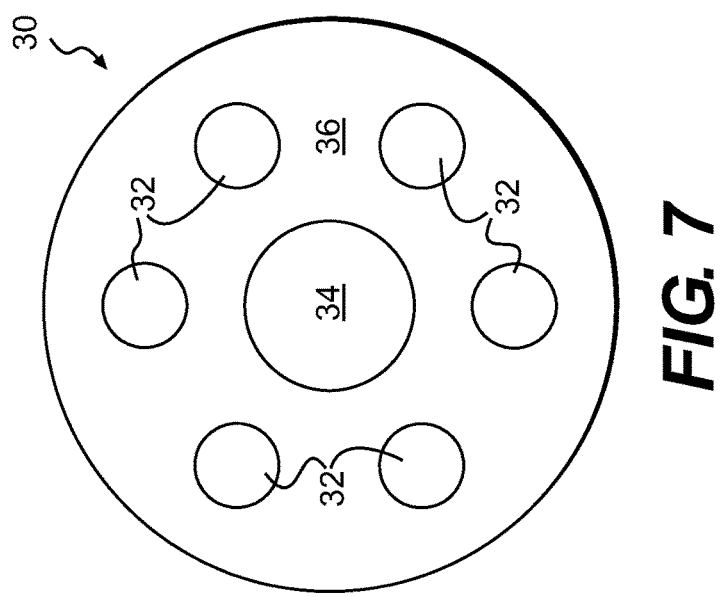
FIG. 7 shows a front view of a manifold for use in the device of the invention.

Another possibility is to pass the proximal end of tubes 8 through a manifold 30, such as that shown in FIG. 7, and allow tubes 8 to slide within manifold 30 in order to provide the required slack. In another embodiment, tubes 8 are rigidly attached to manifold 30 and manifold 30 is movable to provide the required slack.

A variety of different types of radiation sources may be employed. Any suitable, conventional source may be employed. For example, a wire source or a catheter-mounted source may be employed. Radioactive seeds may be attached to a device suitable for advancement through lumens 7, 18 for delivering the brachytherapy. Exemplary radiation sources that may be employed are described in U.S. Pat. Nos. 5,199,939 and 4,282,781, and pending U.S. patent application Ser. No. 09/858,366, the disclosures of which are hereby incorporated by reference for the purpose of describing the details of a suitable radiation source. In a preferred embodiment the radiation source is made of iridium-192. However, other suitable radioactive isotopes may be used such as palladium-103, iodine-125, cesium-131, rhenium-183, tungsten-181, thulium-170, ytterbium-169, terbium-161, dysprosium-159, gadolinium-153, samarium-145 and xenon-127.

FIG. 2 shows a cross-sectional view of proximal portion 4 taken along the line II-II of FIG. 1. Balloon catheter 10 is provided with an internal lumen 18 and an inflation lumen 25 that are together defined by a tube 19. Inflation lumen 25 is used for inflating balloon 14 of balloon catheter 10. Inflation lumen 25 is provided with a barrier 26, such as a check valve, luer actuated valve, or other suitable means, which permits inflation of balloon 14 via inflation lumen 25, when in an open position, and which retains fluid in balloon 14 when in a closed position. Barrier 26 is also adapted to open to permit deflation of balloon 14 at the end of the procedure in order to facilitate removal of balloon catheter 10 from the surgical or body cavity. Balloon catheter 10 is typically inflated by filling balloon 14 with a saline solution 9 in order to inflate the balloon 14 once it is located in the cavity left by the lumpectomy. Additional means for inflation may be used including contrast media for increased visibility, gels with a proper viscosity, as well as some types of soft, natural or synthetic rubbers, elastomeric materials, small pellets, spheres, granules, powders, suspensions, gas generated from chemical reactions, and foams. Alternatively, the fluid inflation mechanism may include a syringe, a gel dispensing tube, or similar, conventional apparatus. The fluid inflation mechanism may be integrated into the device, or it may be provided as a separate device. In a preferred embodiment, balloon 14 is inflated until it compresses at least some of the tissue margins in the cavity.

Internal lumen 18 may be used for a variety of different purposes. Internal lumen 18 could be used for insertion of a guide wire or stiffening spine, for example, should these be required for a particular procedure. Alternatively, a radiation source may be inserted via internal lumen 18 as part of the treatment procedure. In an alternative embodiment, inflation lumen 25 and internal lumen 18 are formed as a single lumen, which may be used both for inflation of balloon 14 and insertion of a radiation source or other device. In this embodiment, barrier 26 can be selected to allow a radiation source to pass through without permitting back flow of fluid out of balloon 14, or, barrier 26 can be advanced to a location closer to distal portion 6 such that it would not be necessary to pass the radiation source through barrier 26 in order to insert it into the single central lumen to deliver a dose of radiation to the patient.

FIG. 3 shows a view of a breast after a lumpectomy has been performed with balloon catheter 10 of FIGS. 1-2 inserted and inflated in the cavity left by the lumpectomy. From FIG. 3 it is apparent that the tissue boundary 28 that forms the cavity 29 left by the lumpectomy is typically non-uniform in shape. As a result, there is a need to customize the radiation dose delivered to the tissue to take into account not only the non-uniform shape of the cavity, but also to ensure that high-risk areas are sufficiently irradiated and that other healthy tissue receives the least possible radiation dose to prevent or minimize undesirable tissue damage. This is a very significant aspect of the present invention since prior art balloon catheters are generally only employed in a small portion of procedures because of the significant drawback that these devices offer either no ability, or at best, a limited ability to customize the radiation dose. As a result, doctors often opt for alternative treatment methods due to the risk of substantial tissue damage and/or insufficient irradiation of the high-risk tissue that is encountered with prior art devices.

Figure 5:
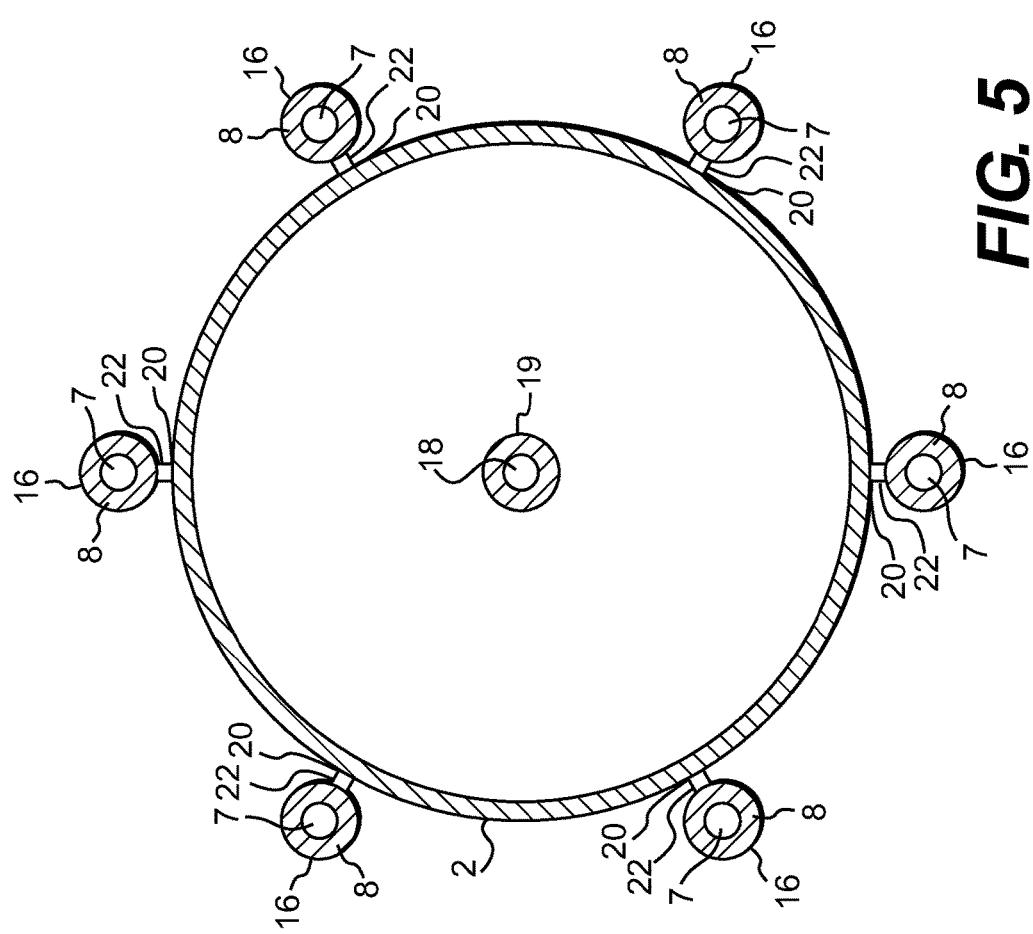
FIG. 5 is a cross-sectional view taken along V-V of FIG. 4.

As shown in FIG. 3, proximal portion 4 of balloon catheter 10 is adapted for attachment to a device for filling the balloon, such as a syringe or other suitable pumping or transfer device. A syringe may be employed to fill balloon 14 with saline solution via inflation lumen 25, as shown in FIG. 5, and/or may be employed to after load one or more radioactive sources into source lumens 7 and/or internal lumen 18, as shown in FIG. 5, particularly if the radioactive source is to be provided as a fluid. Any suitable, conventional afterloader may be employed with the device of the present invention, such as those that are commercially available from Nucletron B.V. (Netherlands) and Varian Medical Systems, Inc. (Palo Alto, Calif.). Proximal portion 4 may be connected to an afterloader using a manifold connector similar to the manifold 30 depicted in FIG. 7 below.

Figure 4:
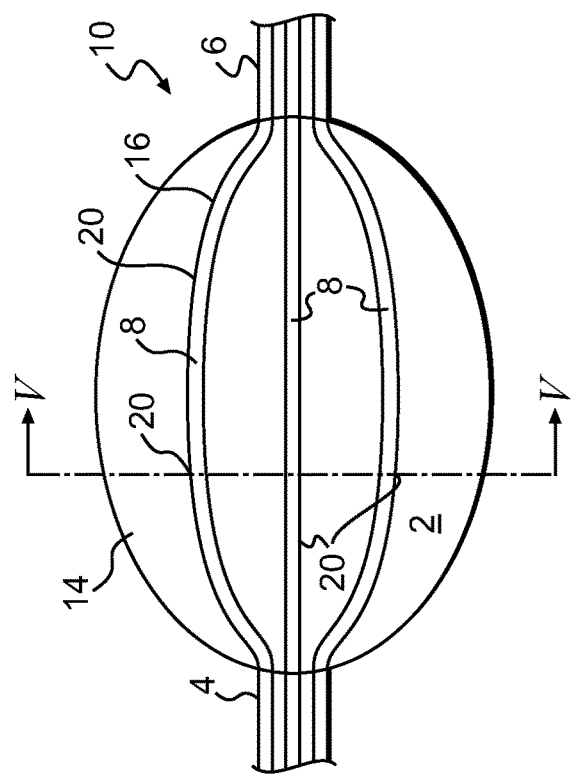
FIG. 4 shows a side view of an alternative embodiment of an expanded device with the tubes attached to the movable surface portion.

FIGS. 4-5 show an alternative embodiment of balloon catheter 10. In this alternative embodiment, tube surface 16 of each tube 8 may be attached to movable surface portion 2 of balloon 14 via a flexible attachment 22. The entire length of tube surface 16 may be attached to movable surface portion 2 from proximal portion 4 to distal portion 6 via flexible attachment 22. Alternatively, tube surface 16 may be attached at one or more attachment locations 20 located on movable surface portion 2 of balloon 14 via flexible attachments 22. In FIG. 4, tube 8 is shown attached to movable surface portion 2 at two attachment locations 20 via flexible attachments 22. Alternatively there could be more or less attachment locations 20. Flexible attachments 22 may be fabricated from a material that is more flexible than the material employed to fabricate tubes 8. Tubes 8 may be made from a relatively rigid, crush-resistant material that allows radial bending of tubes 8, as shown in the inflated position of FIG. 1, but tends to resist deformation of tubes 8 in a manner that prevents or minimizes deformation of source lumens 7. Since flexible attachments 22 are more flexible than tubes 8, flexible attachments 22 will preferentially deform, e.g. by stretching, during inflation of balloon 14, to thereby retain tubes 8 in close proximity to movable surface portion 2, without causing substantial deformation of tubes 8 or source lumens 7. Tubes 8 may also incorporate directional strengthening or stiffening ribs in order to maintain radial positioning about the surface of the movable surface portion.

Other suitable means for attaching tubes 8 to movable surface portion 2 may also be employed. For example, tubes 8 may be formed integrally with movable surface portion 2, though this embodiment is less preferred since it may result in some deformation of tube 8 and hence source lumens 7 during inflation of balloon 14. Generally, the means for attaching tubes 8 to movable surface portion 2 allow some movement of tubes 8 relative to movable surface portion 2 such that deformation of tubes 8 thereby deforming source lumens 7, as a result of the inflation of balloon 14, is prevented or minimized. It is also within the scope of the present invention to apply a combination of flexible attachments 22 and loops 12.

Figure 6:
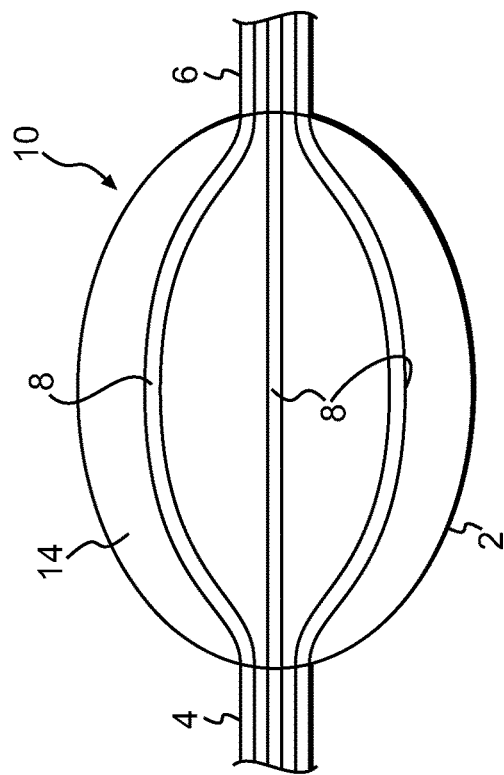
FIG. 6 shows a side view of an alternative embodiment of an expandable device with lumens attached only to proximal and distal portions of the device.

FIG. 6 shows another alternative embodiment wherein tubes 8 are not secured to movable surface portion 2, but rather are only attached to distal and proximal portions 4, 6 of device 10. This embodiment provides the most flexibility to tubes 8. In this embodiment, tubes 8 can be fabricated from a relatively rigid material and are sized such that tubes 8 form a substantially tight fit with movable surface portion 2 when balloon 14 is inflated, or incorporate directional stiffening ribs, in order to best locate tubes 8 at a predetermined location relative to the longitudinal axis of balloon catheter 10. While it is preferable to provide some additional stability to tubes 8 by securing tubes 8 to movable surface portion 2 as described above, thereby ensuring that tubes 8 are always located substantially precisely at a predetermined location relative to the longitudinal axis of balloon catheter 10, other means such as material selection or tube geometry and directional strengthening or stiffening ribs can be employed if desired.

FIG. 7 shows a front view of a manifold 30 which can form part of a manifold connector for connecting proximal portion 4 to an afterloader, or manifold 30 may be used to secure tubes 8 in position relative to proximal portion 4 of balloon catheter 10. Manifold 30 includes a structure 36 that defines passages 32 for receiving tubes 8 of the balloon catheter 10. Structure 36 also defines a central lumen 34 through which can be passed, for example, a central tube 19 housing the inflation lumen 25 and internal lumen 18. Central lumen 34 can alternatively form an integral part of a combined inflation and internal lumen, when the inflation and internal lumens are combined in a single lumen, as described above. Manifold 30 can be employed to provide slack in tubes 8 as described above. For example, tubes 8 can be inserted through passages 32 and be allowed to freely move relative to manifold 30 to provide the required slack. Alternatively, tubes 8 may be affixed to manifold 30 and manifold 30 may be movable relative to the device 10 to provide the required slack in tubes 8. In another embodiment, manifold 30 is of sufficient thickness that passages 32 have sufficient length to permit tubes 8 to slide some distance within passages 32, without disengaging from manifold 30, to provide the required slack in tubes 8.

In one embodiment, a combination of the manifold 30, a plurality of tubes 8 and a distal attachment portion can be provided as a separate device that can later be combined with an inflatable balloon inserted through central lumen 34 in manifold 30. This would provide the ability to use several different sized and/or shaped balloons provided with a plurality of external source lumens 7 formed by the plurality of tubes 8 of various geometries as described above associated with manifold 30.

The brachytherapy device of the present invention has been described above with reference to several different embodiments of balloon catheters 10. However, the device need not be a balloon catheter. For example, movable surface portion 2 can be provided by a movable or expandable mechanical device, rather than being formed by an inflatable balloon. One suitable device is shown in FIGS.

8A-8D. As shown, the device can include a cylinder 100 having a proximal end 101 and being formed from several distinct surface portions 102 that are attached to one another by, for example, hinges 104. The cylinder 100 is shown in the unexpanded position in FIGS. 8A and 8C and in the expanded position in FIG. 8B. Cylinder 100 is provided with an opening 106 that leads to an inner chamber defined by interior surfaces 108 into which a conical expander 110 may be inserted in order to expand the surface portions 102 by contact between the outer surface 111 of conical expander 110 and interior surfaces 108 as the conical expander is passed through opening 106. Thus, the further that the conical expander 110 is inserted into the inner chamber defined by interior surfaces 108, the greater the expansion of the cylinder 100 since outer surface 111 of conical expander 110 will force the surface portions 102 outward by exertion of force on interior surfaces 108 of cylinder 100. In this manner, the movable surface portions 102 of the device are actuated by a simple mechanical means, rather than by an inflatable balloon. This device can be provided in a variety of shapes, other than cylindrical, to meet the requirements for a particular treatment. Other, conventional devices that provide movable surface portions can also be employed.

Figure 9:
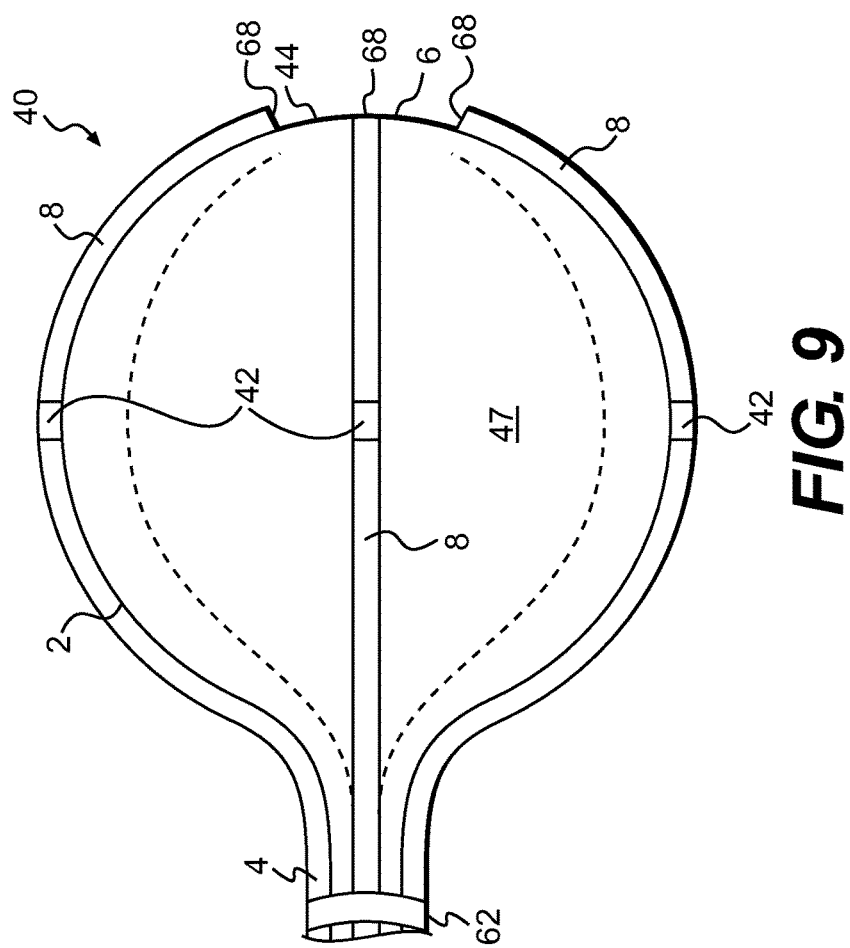
FIG. 9 shows a side view of an expandable device provided with an attachment sleeve for attachment of the expander to the expandable surface portion.

FIG. 9 shows a side view of expandable device 40 in an expanded state and having a proximal portion 4 and a distal portion 6. Expandable device 40 includes an expandable structure 47 that forms an expandable surface portion 2 and has an interior surface 3. Expandable device 40 is provided with a plurality of attachment sleeves 42 which are secured to expandable surface portion 2 of expandable structure 47. A plurality of flexible tubes 8 are secured to the expandable structure 47 via attachment sleeves 42 in a manner whereby tubes 8 can slide within attachment sleeves 42 to provide for relative movement between tubes 8 and expandable structure 47.

Tubes 8 extend along the expandable surface portion 2 and terminate at distal end 6 of expandable device 40. Tubes 8 may be provided with tube end plugs 68 to prevent wire 41 or source 43 from exiting distal ends of tubes 8 during treatment and to prevent body fluids from entering lumens. At distal end 6 of expandable device 40, there may be provided an attachment membrane 44 to which tubes 8 may be attached in any suitable manner. Attachment membrane 44 is, in turn, secured to central tube 19, shown in FIGS. 10A-12 to thereby provide structural support to the distal ends of tubes 8.

In the embodiment of FIG. 9, expandable surface portion 2 is not expanded by inflation, but is instead expanded by a mechanical expander. FIGS. 10A-12, discussed in detail below, show three different embodiments of mechanical expanders for use with the expandable device 40, each of which utilizes attachment sleeves 42 shown in FIG. 9.

FIGS. 10A-10B show a longitudinal cross-sectional view of one embodiment of an expandable device 40 as shown in FIG. 9. FIG. 10A shows the expandable device 40 in the unexpanded state and FIG. 10B shows the expandable device 40 in the expanded state. In this embodiment, attachment sleeves 42 are each secured to an equatorial tube spacing belt 56 in any suitable manner, which tube spacing belt 56, in turn, is secured to expandable structure 47. Attachment sleeves 42 operate to both secure tubes 8 to expandable structure 47 and to assist in guiding expansion of expandable structure 47. Tube spacing belt 56 is secured to expandable structure 47 in any suitable manner, such as by being integrally formed with expandable structure 47, or by being bonded, stitched, and fastened, etc. to expandable structure 47.

The mechanical expander of FIGS. 10A and 10B, includes four expander rods 46 each of which is secured at the proximal end 59 thereof to a movable member such as a sliding sleeve 58 by any suitable means such as by affixation of the proximal ends of expander rods 46 in slots 60 provided in sliding sleeve 58. Different numbers of expander rods 46 may be employed. Typically, there will be one expander rod 46 for each flexible tube 8. Distal ends 45 of expander rods 46 are secured to tube spacing belt 56 in any suitable manner such as by insertion into flexible rod receptacles 48 formed integrally with tube spacing belt 56, as shown.

The mechanical expander of FIGS. 10A and 10B operates via the manipulation of sliding sleeve 58 located around central tube 19 in the proximal portion 4 of expandable device 40. During operation of expandable catheter 40, sliding sleeve 58 is moved relative to tube 19 towards distal end 6 of expandable device 40. Moving sliding sleeve 58 forces the proximal ends 59 of rods 46 to move towards the distal end 6 of expandable device 40. Since distal ends 45 of rods 46 are fixed to expandable structure 47, this will cause both expansion of expandable structure 47 and bending of rods 46, as shown. Moving sliding sleeve 58 back away from distal end 6 will reverse the process allowing rods 46 to straighten by virtue of shape memory and allowing expandable structure 47 to return to its unexpanded state. An optional binding ring 62 may be used to secure tubes 8 in an approximately cylindrical shape at the proximal portion 4 of the device 40.

Rod spacing lines 52 are an optional feature that may be used to maintain a desired spacing between rods 46 and central tube 19. Rod spacing line 52 is attached to rods 46 at attachment points 54 and to central tube 19 for the purpose of maintaining a desired spacing between rods 46 and central tube 19 during expansion of expandable device 40. Rod spacing lines 52 are sufficiently flexible that lines 52 can bend to be substantially parallel to central tube 19 when the device 40 is in the unexpanded state. Alternatively, lines 52 may be rigid, in which case lines 52 should be hingedly or flexibly connected to central tube 19 and rods 46 to allow for different angles between lines 52, central tube 19 and rods 46 during expansion of expandable device 40.

Expandable device 40 may be used in the same manner as balloon catheter 10 discussed above in order to treat the tissue in close proximity to a body or surgical cavity. After expansion of expandable device 40, an afterloader is used for inserting a source wire 41 or a source 43 into source lumens 7 and/or internal lumen 18, within tubes 8 and 19 respectively.

The expander shown in FIGS. 10A and 10B can expand the expandable device 40 without the need for an inflation fluid. Thus, central tube 19 does not require an inflation lumen 25 as in the embodiments described above with respect to FIGS. 1-7. Also, the expandable structure 47 need not be fluid tight and thus may take on a variety of alternative forms. For example, expandable structure 47 may be made from mesh, a perforated sheet material or some other fluid permeable structure. However, it is preferable that expandable structure 47 be fabricated in a manner that prevents tissue surrounding the body or surgical cavity from penetrating into expandable structure 47 since this may alter the dose profile in the treatment area and/or complicates removal of the brachytherapy device from the body or surgical cavity.

Figure 11:
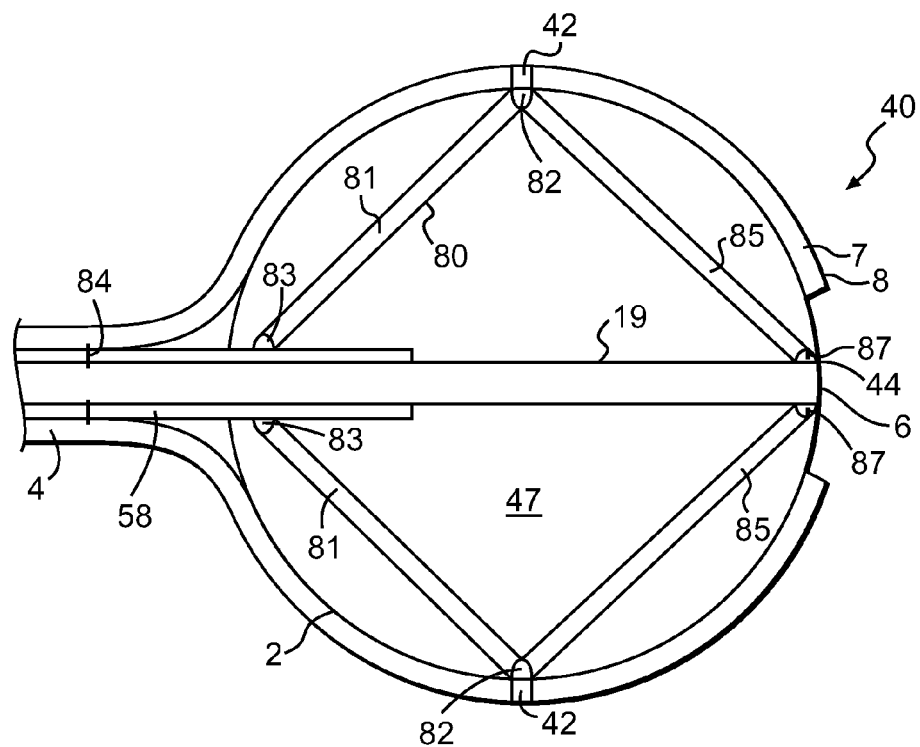
FIG. 11 shows a longitudinal cross-sectional view of another embodiment of the expandable device shown in FIG. 9 employing centrally located linkage arms to expand the expandable surface portion.
Figure 12:
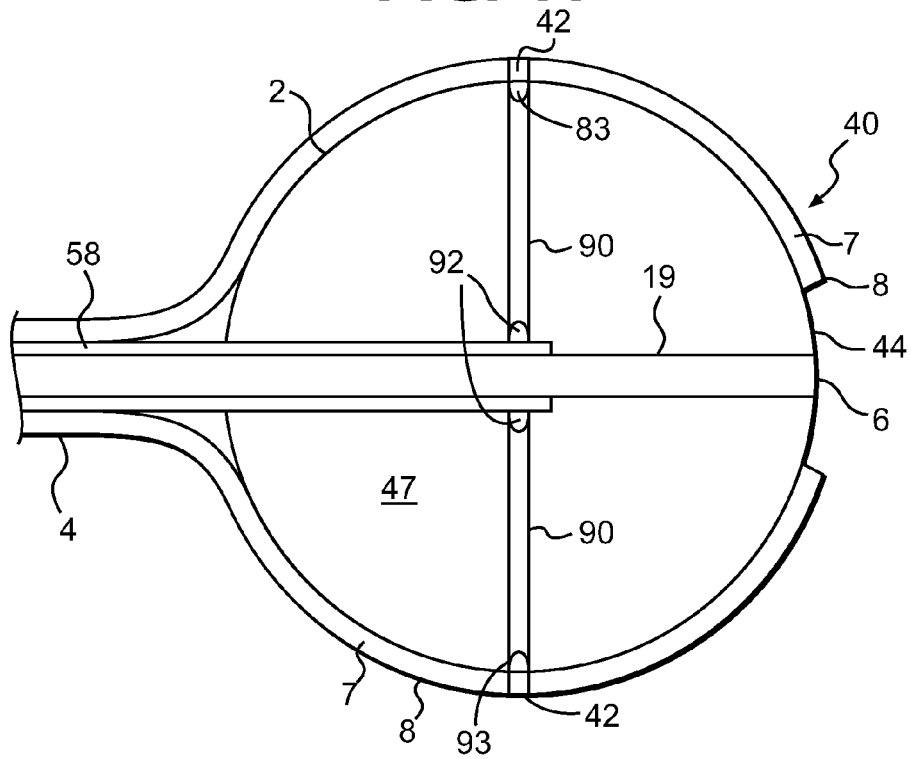
FIG. 12 shows a longitudinal cross-sectional view of yet another embodiment of the expandable device shown in FIG. 9 employing linkage arms to expand the expandable surface portion.

The two embodiments shown in FIG. 11 and FIG. 12 are alternative embodiments of the expandable device 40 of FIG. 9 which use linkage arms 80, rather than expander rods 46, in order to expand expandable structure 47. Alternative expansion mechanisms using various conventional forms of linkage arms are also possible. Linkage arms 80 may be constructed of plastic, metal, carbon fibers, ceramics, super-elastics, shape memory materials, etc. Linkage arms 80 secure and guide tubes 8 during expansion of expandable structure 47 as a result of the attachment of linkage arms 80 to expandable structure 47 via pivot points 82 located at the locations of attachment sleeves 42. Linkage arms 80 are attached at their proximal ends 81 to slidable sleeve 58 via additional pivot points 83, and at their distal ends 85 to the distal portion 6 of expandable device 40 via additional pivot points 87. Pivot points 87 may be attached to central tube 19, as shown.

During operation of the embodiment shown in FIG. 11, sliding sleeve 58 is moved towards distal end 6 of expandable device 40 from a first position to a second position. Sliding sleeve 58 is also connected to tubes 8 via tube connecting member 84. Moving sliding sleeve 58 towards distal end 6 causes linkage arms 80 to pivot about pivot points 83, 87 at pivot points 82. This causes pivot points 82 to move outwards to the position shown in FIG. 11 to thereby expand the expandable structure 47.

In the embodiment shown in FIG. 12, rigid linkage arms 90 are attached at one end to sliding sleeve 58 via pivot points 92 and are attached to expandable structure 47 at the locations of attachment sleeves 42 via pivot points 93. Rigid linkage arms 90 secure and guide tubes 8 via attachment sleeves 42 during the expansion of expandable structure 47.

During the operation of the embodiment shown in FIG. 12, sliding sleeve 58 is moved towards distal end 6 of expandable device 40 from a first position to a second position. Moving sliding sleeve 58 towards distal end 6 causes rigid linkage arms 90 to pivot about pivot points 92, 93 and thereby cause expansion of the expandable structure 47.

Figure 13:
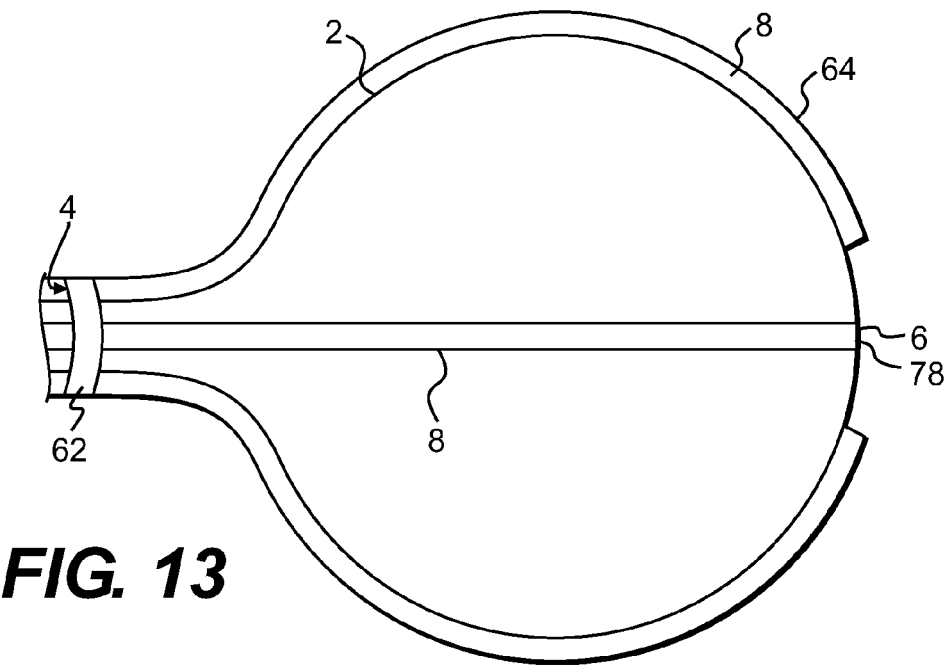
FIG. 13 shows a side view of another embodiment of an expandable device provided with internal expansion means to expand the expandable surface portion.
Figure 15:
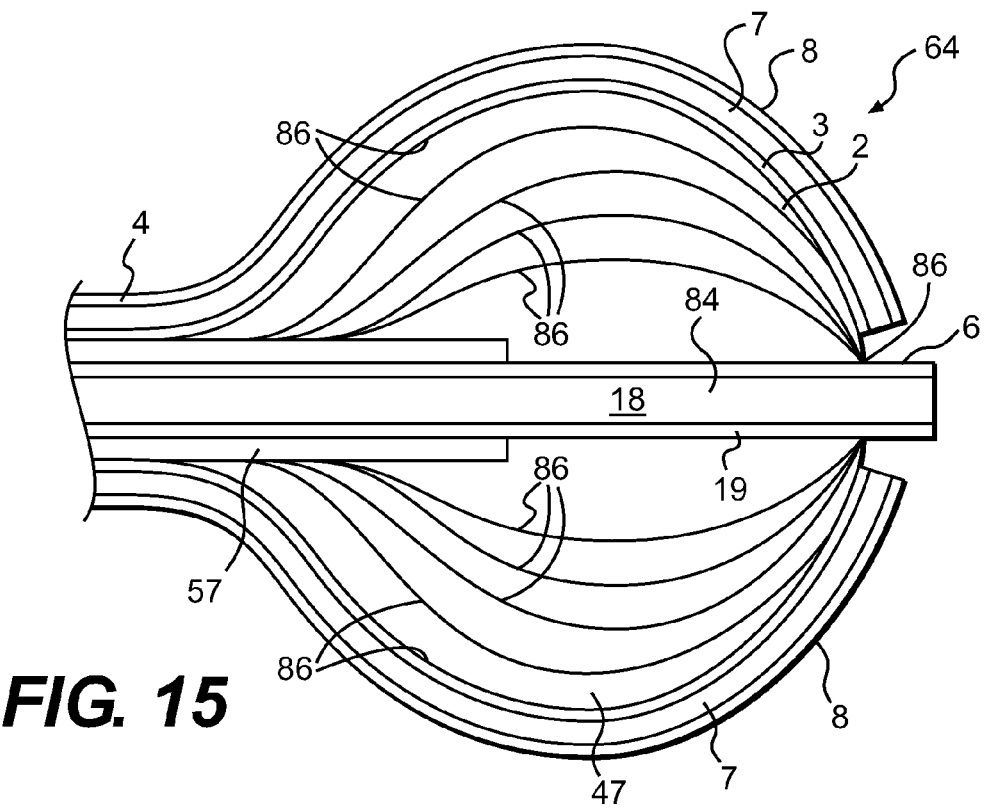
FIG. 15 shows a longitudinal cross-sectional view of another embodiment of the expandable device shown in FIG. 13 employing a wire mesh to form the expandable surface portion.
Figure 14:
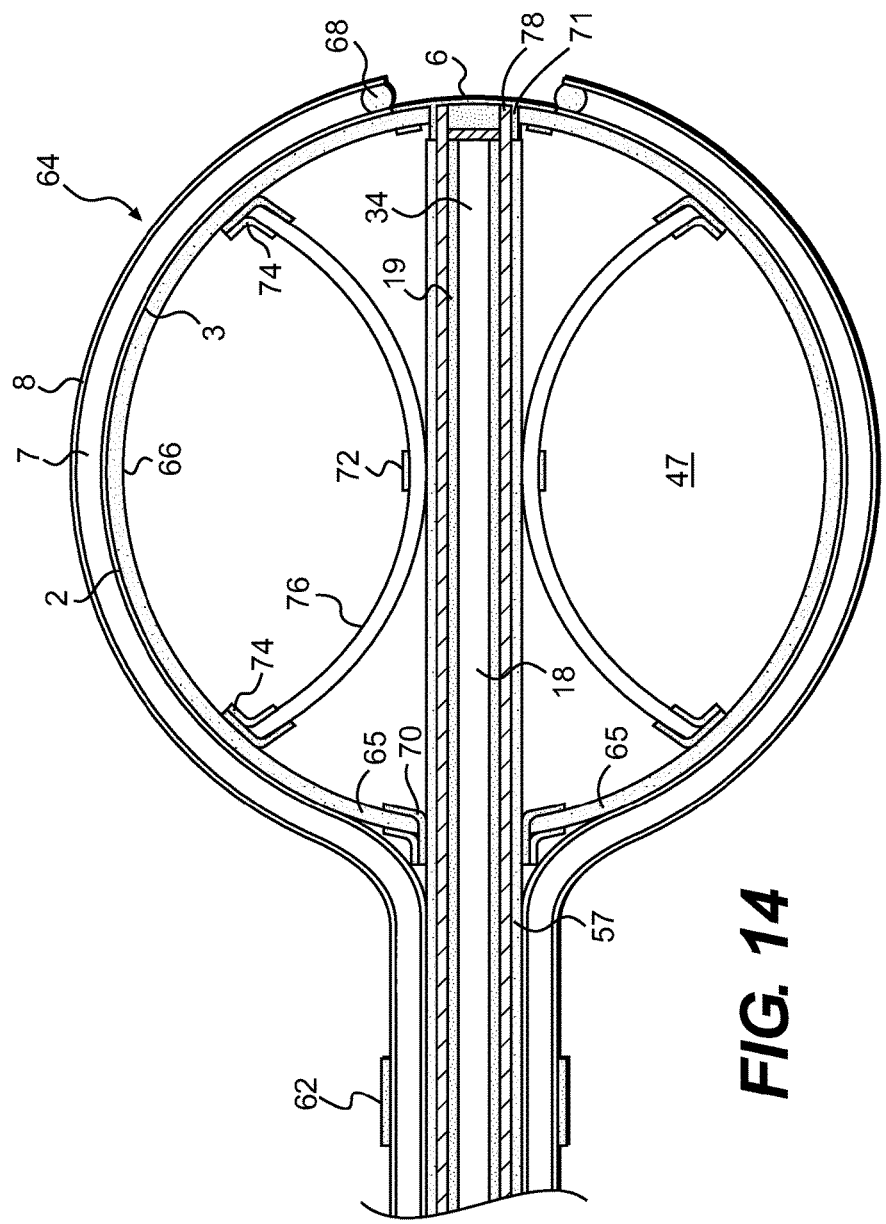
FIG. 14 shows a longitudinal cross-sectional view of one embodiment of the expandable device shown in FIG. 13 employing flexible rods to expand the expandable surface portion.

FIG. 13 shows a side view of an expandable device 64 where tubes 8 are secured directly to outer surface 2 of expandable structure 47. Expandable device 64 is not inflated and is instead expanded with an internal mechanical expander. FIGS. 14 and 15, discussed in detail below, show alternative embodiments of mechanical expanders for use with expandable device 64 of FIG. 13.

FIG. 14 shows a cross-sectional view of one embodiment of an expander for the expandable device 64 shown in FIG. 13. The expander of FIG. 14 includes a plurality of support rods 66 attached to a sliding sleeve 57 via flexible attachments which may be flexible attachment receptacles 70, as shown in FIG. 14. Flexible attachment receptacles 70 enable the proximal ends 65 of support rods 66 to be positioned at different angles relative to sliding sleeve 57 during the expansion process, while remaining attached to sliding sleeve 57. Thus, in the unexpanded state, proximal ends 65 of support rods 66 may be substantially parallel to the longitudinal axis of sliding sleeve 57. In the expanded state, shown in FIG. 14, proximal ends 65 of support rods 66 may be substantially perpendicular to the longitudinal axis of sliding sleeve 57. At distal end 6, support rods 66 are secured to a distal attachment fitting 78. Distal attachment fitting 78 includes a central tube attachment portion 71 for supporting the distal end of central tube 19. Sliding sleeve 57 may extend the length of central tube 19 in order to provide additional support for expandable device 64 during the process of expansion.

Expansion is accomplished by moving sliding sleeve 57 towards distal end 6 to cause support rods 66 to bend away from central tube 19, as shown in FIG. 14. Attached to expandable support rods 66 is a loose thin film, mesh or similar material, which forms expandable structure 47. Once expanded, binding ring 62 is used to secure sliding sleeve 57 and tubes 8 in place for after-loading.

As shown in FIG. 14, optional secondary support rods 76 can be used in order to provide additional structural support during the mechanical expansion. Secondary support rods 76 are attached to support rods 66 via flexible attachment receptacles 74 and are secured to sliding sleeve 57 via sleeve attachment portions 72. Flexible attachment receptacles 74 enable secondary support rods 76 to flexibly move during the expansion of expandable structure 47. Sleeve attachment portions 72 act to secure and guide secondary support rods 72 so that they assist in providing structural support to the support rods 66 so that a substantially spherical shape is achieved when expandable structure 47 is fully expanded.

The nature of the means for expansion in expandable device 64 shown in FIG. 14 permits expandable device 64 to be expanded without the need for an inflation fluid. This enables the usage of thin film membrane or a mesh for the expandable structure 47 that may have reduced radiation attenuation properties and which need not be fluid tight. The mechanical means used for expanding expandable device 64 means that central tube 19 does not require an inflation lumen 25.

FIG. 15 shows a cross-sectional view of the expandable device 64 shown in FIG. 13. In the embodiment shown in FIG. 15, wire mesh 86, which can also be a cage or slit tubing, is expanded from a cylindrical shape that loosely conforms to the shape of central tube 19 to the spherical shape shown in FIG. 15. Wire mesh 86 is attached to sliding sleeve 57 at its proximal end 89 and to central tube 19 at its distal end. Wire mesh 86 is constructed from a rigid plastic material or tempered metal, super-elastic, or a shape memory material that is flexible enough to bend, but rigid enough to be able to expand expandable structure 47 to form a substantially spherical shape. Alternatively, other geometries may be formed instead of a sphere depending on the needs of treatment and/or cavity shape. Other shapes may include, for example, pear-shaped, elliptical, triangular, rectangular, irregular, or cylindrical.

In order to expand wire mesh 86 sliding sleeve 57 is moved towards distal end 6 of expandable device 64 to thereby exert pressure on the proximal end 89 of wire mesh 86 thereby causing wire mesh 86 to bend from a substantially straight configuration to the curved configuration shown in FIG. 15, thereby expanding expandable structure 47.

Figure 16A:
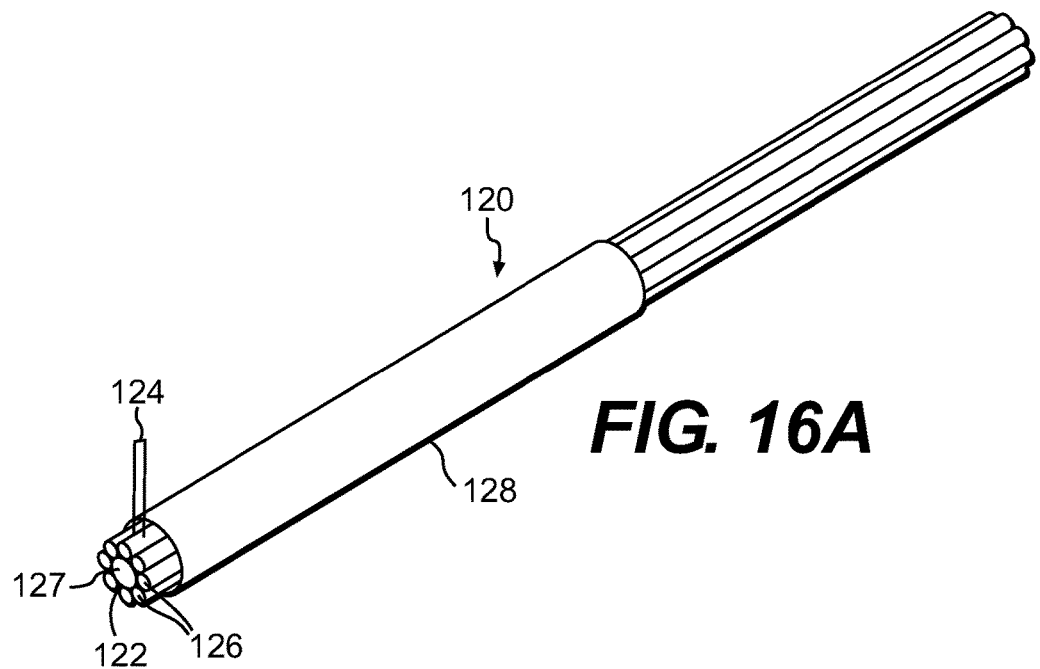
FIGS. 16A-16B show another embodiment of an expandable device which employs a shape memory material, in the unexpanded and expanded positions, respectively.
Figure 16B:
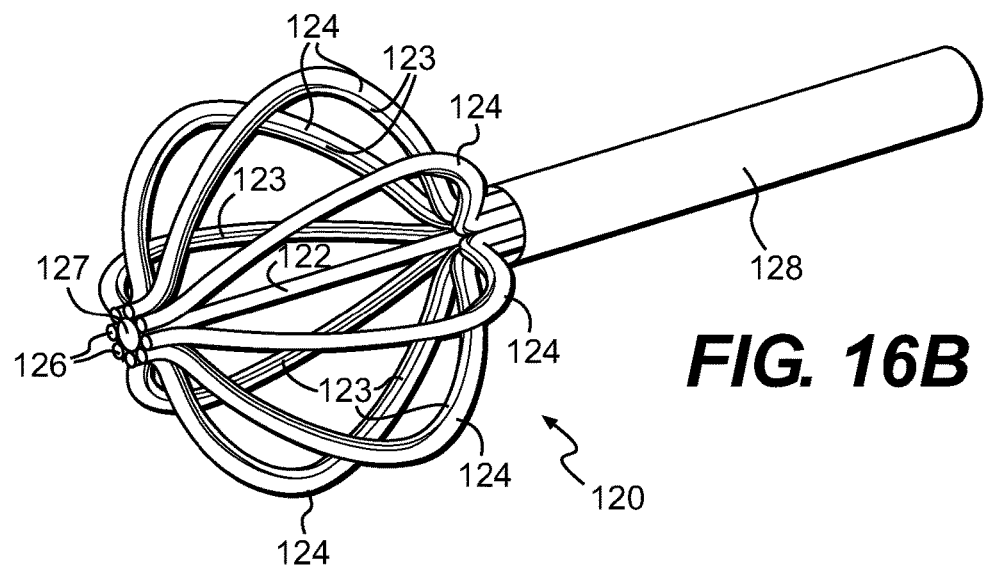
Figure 17A:
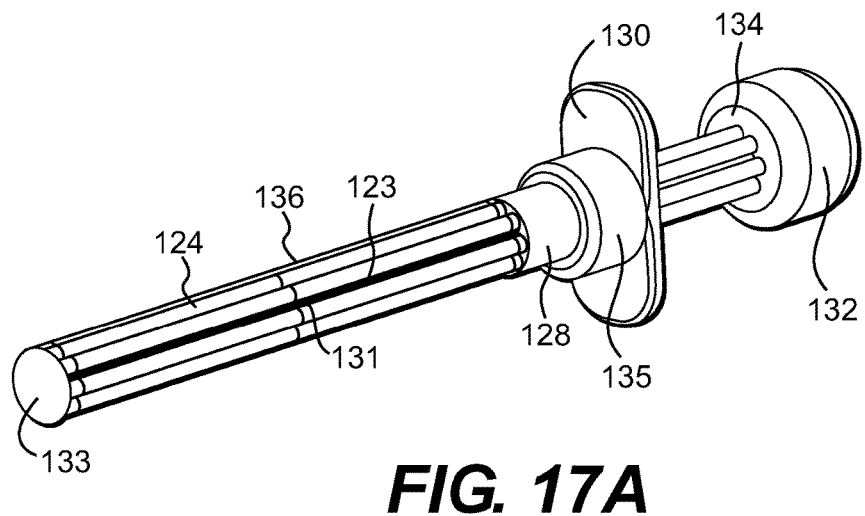
FIG. 17A shows an isometric view of another embodiment of an expandable device in non-expanded position.
Figure 17B:
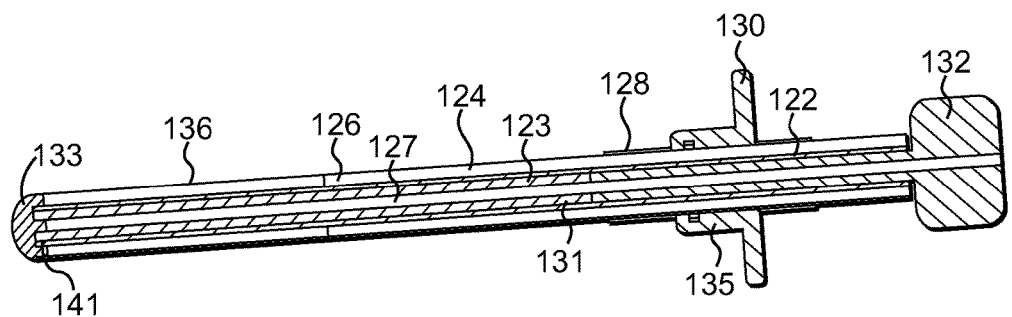
FIG. 17B shows a cross sectional view of the device shown in FIG. 17A.
Figure 17C:
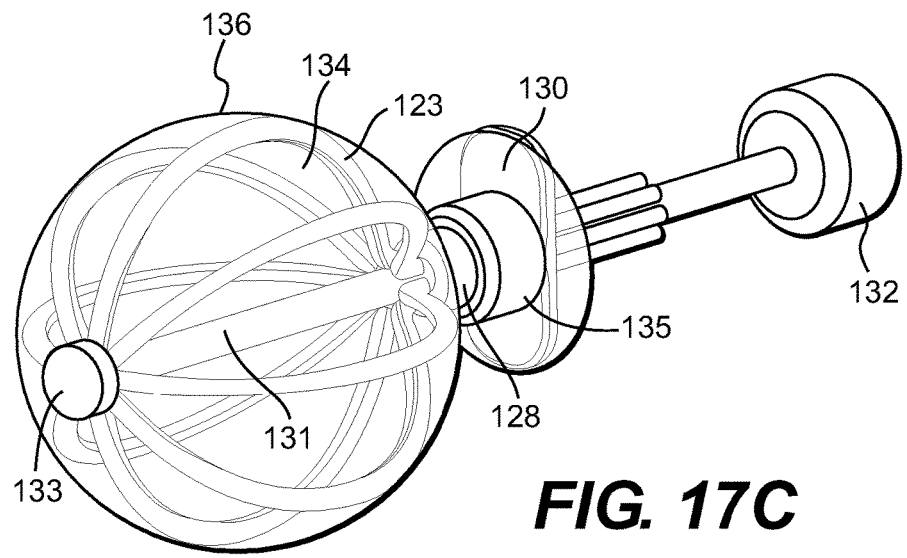
FIG. 17C shows an isometric view of another embodiment of an expandable device in an expanded position.
Figure 17D:
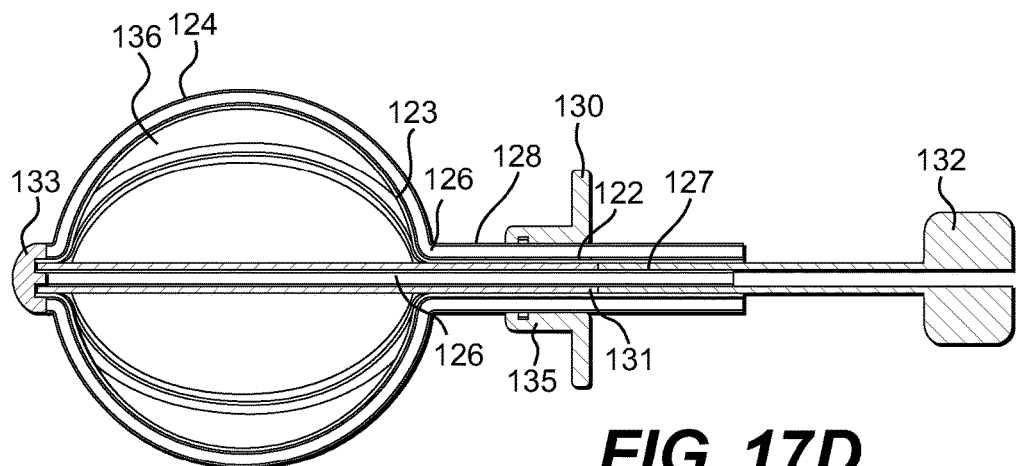
FIG. 17D shows a cross section view of the expanded device shown in FIG. 17C.

In the various embodiments discussed above, the movable member is described as a slidable sleeve 57, 58 that moves towards the distal end 6 of the expandable device 40, 64 from a first position to a second position in order to effectuate expansion of the expandable structure 47. It is to be understood, however, that various other types of movable members may be employed in the context of the present invention. For example, similar results can be achieved by constructing the structure such that the movable member moves away from the distal end 6 of expandable device 40, 64 to effectuate expansion of expandable structure 47. Also, different types of movable members may be employed, other than a slidable sleeve. For example, the movable member may be cylindrical device in an embodiment where no central tube is employed. The movable member may also be in the form of a plurality of finger-like elements, each of which engages the proximal end of the support rod. Other variations on the shape and structure of the movable member are possible, so long as the movable member engages and exerts force on the proximal ends of the support rods to cause expansion of the expandable structure Likewise, the same device may naturally reside in the expanded form and the movable structure may be employed to exert force to return the shape of the device to a cylindrical form, for example. Referring now to FIGS. 16A-16B, there is shown another embodiment of a device in accordance with the present invention that employs a shape memory material, such as nitinol. As shown in FIG. 16A, the device 120 includes an inner tube 122 of shape memory material that has been heat treated to provide the desired shape memory, in this case a hemispherical shape as can be seen in FIG. 16B. Mounted on the outside of inner tube 122 are a cap 133 and a plurality of semi-rigid or flexible tubes 124, each of which defines a source lumen 126 there through. The inner tube 122 and flexible tubes 124 are confined within an outer tube 128 which may be made from a relatively rigid, biocompatible material such as titanium, stainless steel and other conventional materials. Inner tube 122 may be formed by providing a tube-shaped shape memory material, laser cutting the tube into a plurality of expandable arms 123 by cutting slots between the arms 123 and heat treating the arms 123 to provide the desired shape, e.g. hemispherical in this case.

The device 120 is inserted into the surgical or body cavity in the unexpanded state shown in FIG. 16A. Once the device 120 is positioned in the surgical or body cavity, outer tube 128 is retracted in the proximal direction to the position shown in FIG. 16B, whereupon expandable arms 123 expand to the hemispherical position shown in FIG. 16B by virtue of their shape memory characteristics. This causes tubes 124 to also take a hemispherical shape thereby positioning source lumens 126 closely adjacent to the tissue to be treated. To allow tubes 124 to conform to the shape of expandable arms 123 in the expanded position, slack may be provided in tubes 124 at the proximal end in any of the manners described above with respect to other embodiments of the device of the present invention. Once the treatment is completed, the outer tube 128 may be returned to its original position to return the device to the unexpanded state of FIG. 16A for retraction of the device from the body or surgical cavity. Optionally, inner tube 122 may define a central source lumen 127. The inner tube 122 may move in relation to the expandable arms 123 during expansion of the device 120 causing the central source lumen 127 to axially shorten (relative to the spherical portion) during expansion.

Expandable arms 123 may be covered by a film, mesh or balloon, not shown, located between expandable arms 123 and flexible tubes 124 to thereby provide a continuous movable surface portion, if desired for a particular treatment.

FIGS. 17A-17D show alternative embodiments that are similar to the embodiments shown in FIGS. 16A-16B. The embodiment shown in FIGS. 17A-17D includes finger grips 130, plunger 132, and anchoring cap 135. The expansion and contraction of the device is controlled by central control rod 131, shown in FIG. 16B. Central control rod 131 may define a central lumen 127 which can be used as an additional source lumen during the treatment procedure. Central control rod 131 is attached to expandable arms 123 via cap 133. Expandable arms 123 can be formed by partially or wholly splitting a tube, for example, by laser cutting or other similar processes.

Once in the surgical cavity, outer tube 128, which functions like a manifold, is fixed and can temporarily be held in place using finger grips 130. Outer tube 128 may also be provided with indicia identifying one or more of the flexible tubes 124. Finger grips 130 can be removable or non-removable. Central control rod 131 is fixed to cap 133, but is free to slide axially inside outer tube 128. To cause expansion of expandable arms 123, central control rod 131 is retracted in the proximal direction to the position shown in FIGS. 17C and 17D using plunger 132. This moves the expandable arms 123 to the expanded position shown in FIGS. 17C and 17D since the distal ends of expandable arms 123 are captured in corresponding slots 141 in cap 133. Then control rod 131 may be locked in position via a locking mechanism facilitated by friction, interference, rotation, an expanding collar, a thread, or other appropriate, conventional locking mechanism.

Optionally, a strain relief piece, not shown, with a predetermined radius can be employed at the proximal and/or distal end of the device to keep flexible tubes 124 from kinking. Plunger 132 can be removable or permanently affixed, and/or flexible or rigid. Plunger 132 can be in the form of a hand controlled rod, a kinematic mechanism, a pneumatic mechanism, or other device employing mechanical advantage that can operate via being pushed, pulled, twisted, or bent.

Between inner tube 122 and flexible tubes 124 can be a membrane 134 made of woven mesh or polymeric material to help sculpt tissue in the body or surgical cavity. This membrane can be either elastic or flexible. The membrane can also be either liquid-tight or breathable.

Finger grips 130 can also act as an anchoring cap or flap to restrict motion of the device in and out of the entry site. The anchoring cap 135 could also be a device that slides along the length of outer tube 128 and is then fixed/locked to outer tube 128 and sutured to the skin. Anchoring cap 135, or, alternatively, a flap would restrict motion of the device in and out of the body entry site. This should reduce the rate of infection. In an embodiment using a flap, the flap can be an extruded portion of the shaft.

The entire device can be placed in an outer sheath 136 while in the closed position prior to insertion into the body or surgical cavity. Sheath 136 may be made of an expandable material, for example, elastic, a un-folding sheet (i.e. parachute-like: that opens by unfolding from a tightly folded shape into a conformed shape), or some conformable structure. The sheath 136 would act as a barrier between the device and the body or surgical cavity to limit tissue ingrowth into the device and/or to act as a barrier to retain liquid inside the device. This may reduce irritation to the surrounding skin during treatment and retraction of the device from the body or surgical cavity, as well as provide a spacing structure to reduce the dose gradient in the treatment zone. Sheath 136 may also be made of a bioabsorbable material that could remain in the cavity after the device is removed. The sheath may be coated with an appropriate material to further reduce adhesion to tissue and thereby minimize trauma.

Figure 18B:
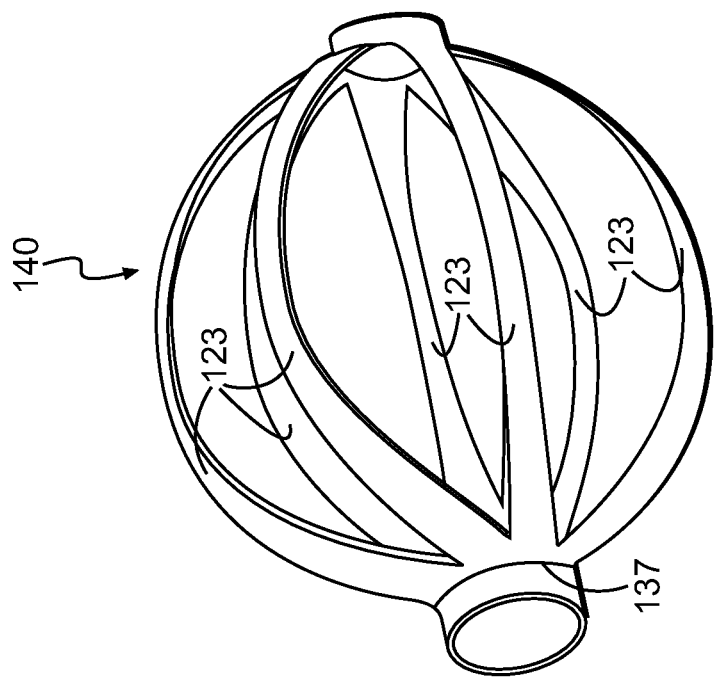
FIG. 18B shows the mechanism in FIG. 18A in an expanded position.
Figure 18A:
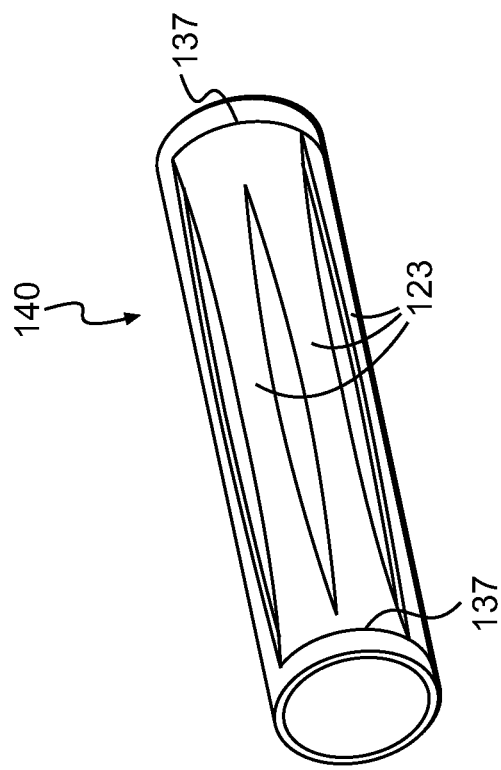
FIG. 18A shows an alternative embodiment of a mechanism for expanding a device.

FIGS. 18A and 18B show an alternative embodiment of expandable arms 123. In this embodiment, expandable arms 123 are hourglass-shaped. Expandable arms 123 of this embodiment, may be made by removing material from tube 140. Tube 140 can be constructed of plastic or a shape memory material such as nitinol. Hinge 137 forms a living hinge that enables expandable arms 123 to expand to form the spherical shape shown in FIG. 18B when actuated by a movable member. In a preferred embodiment, there is a membrane stretched between each expandable arm 123. The membrane can be made of woven mesh or polymeric material to help sculpt tissue in the body or surgical cavity.

This membrane can be either elastic or flexible. The membrane can also be either liquid-tight or breathable.

FIGS. 19A and 19B show an alternative embodiment of expandable arms 123. In this embodiment, expandable arms 123 may be made by making longitudinal slices 139 a tube 140 constructed of thin-walled material such as metal. Hinge 137 is a living hinge that enables expandable arms 123 to expand when actuated by a movable member. FIG. 19B shows a cross-sectional view of the device shown in FIG. 19A.

It is to be understood that in the above examples, non-spherical shapes may also be employed throughout the embodiments and may be controlled as necessary to fill the particular cavity in question. Sophisticated computer programs exist for modeling radiation dosages and dose rates. Such computer programs are currently in use for brachytherapy treatment planning. It is contemplated the device of the present invention, when used in combination with such a treatment planning tool, can provide significant advantages over prior art devices. Specifically, the computer program can be employed to take into account a variety of factors that may affect the treatment such as the shape of the cavity left by the lumpectomy, the distance to the tissue to be treated, the desired depth of tissue irradiation, the existence of areas of healthy or different tissue for which it is desirable to reduce or minimize the radiation dose, etc. Using these parameters, it is possible to create a customized treatment plan that can be carried out using the device of the present invention.

The design of the device of the present invention provides a number of advantageous features that can be exploited in the treatment planning. For example, the location of source lumens 7 on the outside of movable surface portion 2 allows the positioning of the radioactive source in close proximity to the treatment area with a minimal amount of intervening structure and/or fluid reducing the shielding and/or attenuation of radiation by the structure of the device itself. Another significant advantage of the device of the present invention is that it presents a large number of different locations where the radioactive source can be positioned to deliver the radiation dose. Not only can the source be positioned in any of the source lumens or the internal or inflation lumen, but the source can also be positioned at any location along the length of any of these lumens. In addition, different length sources can be employed within the various lumens to alter the dose pattern. Moreover, sources of different activities can be used simultaneously or sequentially in one or more of the lumens to further customize the treatment. In this manner, far more precise dosing can be provided than in prior art brachytherapy devices. As a result, the device of the present invention will be useful in a significantly larger number of procedures, due to the flexibility that it provides in dosing the patient.

The device of the present invention can be customized in various ways for specific patients or treatments. For example, the device may be made in different lengths to accommodate different depths of body or surgical cavities. In addition, the device may be fabricated with different sizes and/or shapes of movable surface portions to accommodate different sized body or surgical cavities. Also, in specific cases it may be possible or desirable to use one or more radiation sources outside the expandable surface portion to provide additional tailoring of the dose profile delivered by the device.

The device of the present invention offers several advantages in use. One important advantage is that it permits a very high degree of dose customization for particular treatment plans. Another advantage is that the device of the present invention can be implanted for lengthy periods without causing a significant disruption in the patient's life to thereby permit treatments over a period of days or even weeks. This advantage is realized because the proximal portion of the device that extends out of the body or surgical cavity can easily be secured and hidden, for example, under the armpit of a breast cancer patient, while the device is implanted. Also, the present invention provides the ability to easily customize the length of the device for body or surgical cavities located at different depths in the body since it is possible to cut the tubes to a desired length for use.

The method for using a brachytherapy device in accordance with the present invention for interstitial treatment of breast cancer will now be discussed. First a lumpectomy is performed on a patient's breast. A surgeon makes a small incision over or near the breast tumor and excises the lump or abnormality along with a margin of appropriate thickness of normal surrounding breast tissue. After the lumpectomy has been performed the patient may now undergo radiation treatment using a brachytherapy device in accordance with the present invention. In standard radiation treatment after a lumpectomy the treatment runs roughly six weeks for standard external beam radiation therapy. Utilizing the device of the present invention, the treatment can usually be shortened to, for example, twice daily for five days. The treatment hyperfractionation of 3.4 Gy b.i.d. (twice daily) for five days (with at least six hours between each fraction) is a clinically derived schedule for accelerated partial breast irradiation. Alternatively, the device of the present invention may be used to provide a boost radiation treatment to the lumpectomy site typically following external beam radiation.

Figure 20:
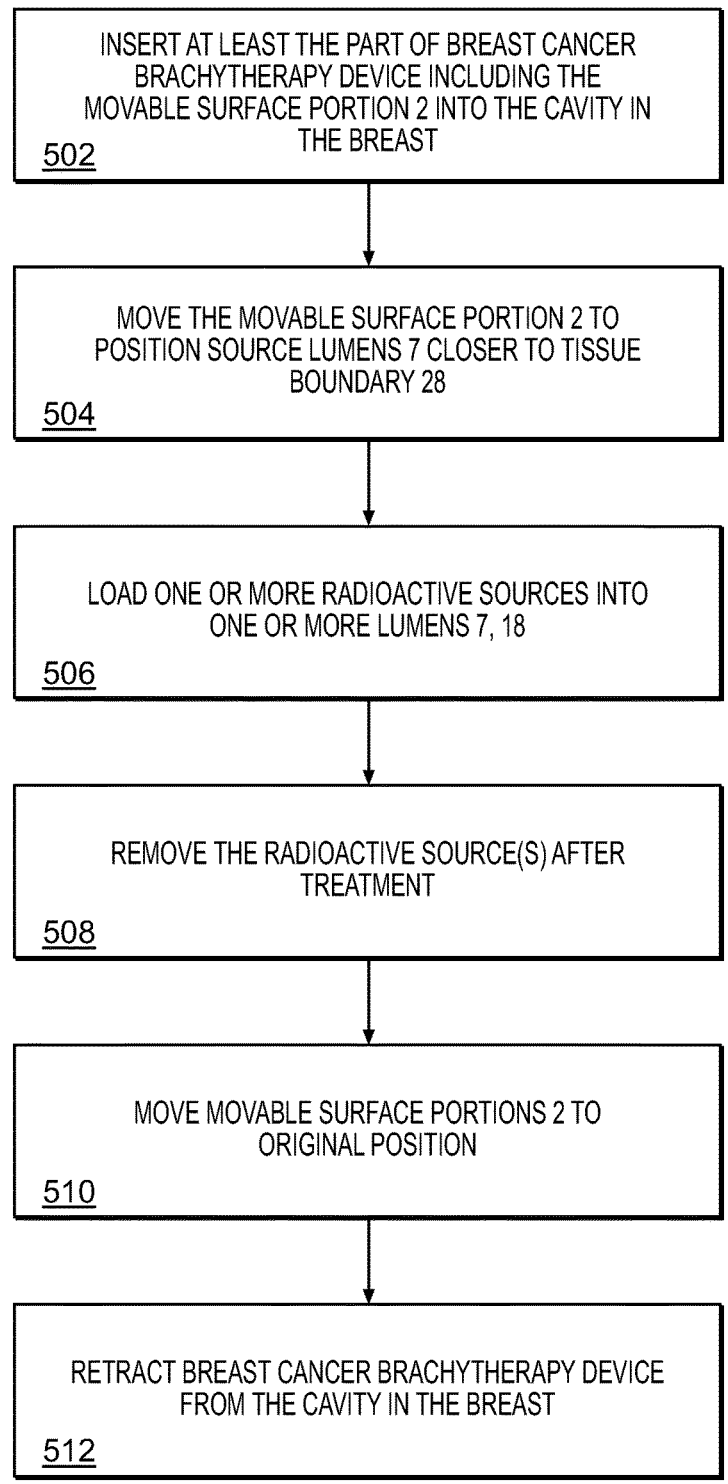
FIG. 20 shows a schematic representation of a method for using a brachytherapy device in accordance with the present invention.

FIG. 20 shows a schematic representation of one method for using a brachytherapy device in accordance with the present invention. At step 502, at least the portion of the brachytherapy device of the invention, including the movable surface portion 2, is inserted via a surgical incision made in the breast into the cavity in the breast that remains after a lumpectomy. At step 504 movable surface portions 2 are moved within the cavity to position source lumens 7 closer to tissue boundary 28.

At step 506 one or more radioactive sources are loaded into one or more lumens 7, 18. Loading may be dictated, for example, by a predetermined treatment plan. Step 506 can involve one or more sub-steps, depending on the complexity of the treatment plan. Also, the same or different sources may be inserted into different tubes 8, at different locations along the lengths of the tubes 8 and/or for different durations, as explained above. At step 508 the one or more radioactive source(s) are removed from lumens 7, 18 to conclude the treatment. At step 510, the movable surface portions 2 are returned to their original position and at step 512 the brachytherapy device is retracted from the body or surgical cavity. Steps 502-512 can be repeated as needed. The method of the present invention may further include an additional step of preparing a treatment plan to be followed in step 506, if desired.

Although use of a brachytherapy device of the present invention has been described in the context of breast cancer brachytherapy, it is to be understood that the various devices of the present invention can be employed in any type of interstitial brachytherapy wherein a device is inserted into a surgical cavity. The device of the present invention may also be employed in intra-cavital brachytherapy in an existing body cavity. For example, the devices of the present invention may be employed for inter-uterine brachytherapy, esophageal brachytherapy, nasal-pharyngeal brachytherapy, rectal brachytherapy, or for treatment after removal of a tumor, cyst, polyp or other mass, thereby creating a surgical cavity.

Although the devices and methods of the present invention have been described with reference to breast cancer brachytherapy, it is to be understood that these devices are applicable for other types of brachytherapy treatment involving insertion of the brachytherapy device into a body cavity or a surgical cavity created by a surgical procedure. These devices or methods may also be employed for the delivery of various drug therapies or diagnostic agents desired for the treatment of various other disease states.

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

The invention claimed is:

1. A brachytherapy device for treating tissue surrounding a body cavity within a patient, comprising:
   a) an elongated shaft having a longitudinal axis and a distal shaft portion and having a plurality of tubular members that extend along the distal shaft portion, the distal shaft portion being configured to be deployed within the body cavity, the plurality of tubular members being configured to be radially off-set from the longitudinal axis at the distal shaft portion to facilitate asymmetric irradiation of the body cavity when the distal shaft portion is deployed within the body cavity, wherein the plurality of tubular members are configured to selectively expand away from the distal shaft portion;
   b) an expandable member coupled to the elongated shaft to define an expandable volume around the distal shaft portion, and wherein the expandable member is configured to be spaced apart from the plurality of tubular members when the plurality of tubular members are expanded; and
   c) a cap located on the distal shaft portion, and a distal end of each of the tubular member is secured in the cap.

2. The brachytherapy device of claim 1, wherein the expandable member is configured to expand separately from the plurality of tubular members.

3. A brachytherapy device for facilitating asymmetrical irradiation of a body cavity, comprising:
   an elongated shaft having a proximal end, a distal end, and a distal shaft portion proximal to the distal end, the elongated shaft having a centrally located longitudinal axis; and
   an expandable member coupled to the elongated shaft to define an expandable volume at the distal shaft portion, the elongated shaft including:
      a plurality of off-set radiation delivery lumens, each off-set radiation delivery lumen of the plurality of off-set radiation delivery lumens having a respective off-set treatment portion radially off-set from the longitudinal axis within the expandable volume defined by the expandable member, and with each off-set radiation delivery lumen of the plurality of off-set radiation delivery lumens being configured to selectively expand away from the longitudinal axis and receive a radiation source and guide the radiation source into the respective off-set treatment portion;
      an inflation lumen coupled in fluid communication with the expandable volume defined by the expandable member, the inflation lumen being configured for connection to an inflation fluid source, wherein the expandable member is configured to be spaced apart from the plurality of off-set radiation delivery lumens when the plurality of off-set radiation delivery lumens are expanded; and
      a cap located on the distal shaft portion, and a distal end of each of the off-set radiation delivery lumens is secured in the cap.

4. The brachytherapy device of claim 3, wherein each respective off-set radiation delivery lumen is configured to slidably hold the radiation source at a selected dwell position within the respective off-set treatment portion.

5. The brachytherapy device of claim 3, wherein the elongated shaft further includes a central radiation delivery lumen having a central treatment portion located within the expandable volume on the longitudinal axis, with each respective off-set treatment portion being radially off-set from the central treatment portion.

6. The brachytherapy device of claim 5, wherein each respective off-set treatment portion and the central treatment portion extends longitudinally across the expandable volume defined by the expandable member.

7. The brachytherapy device of claim 5, wherein each respective off-set treatment portion and the central treatment portion is located at a respective fixed position relative to the longitudinal axis.

8. The brachytherapy device of claim 5, wherein each of the plurality of off-set radiation delivery lumens, the central radiation delivery lumen, and the inflation lumen has a respective proximal portion that extends proximally from the proximal end of the elongated shaft.

9. The brachytherapy device of claim 8, wherein at least the respective proximal portion of each of the plurality of off-set radiation delivery lumens, the central radiation delivery lumen, and the inflation lumen is flexible to facilitate movement of the respective proximal portion relative to the elongated shaft.

10. The brachytherapy device of claim 5, comprising three off-set treatment portions equally disposed around the central treatment portion.

11. The brachytherapy device of claim 3, comprising multiple off-set treatment portions equally disposed around the longitudinal axis.

12. The brachytherapy device of claim 3, wherein the expandable member is a balloon.

13. The brachytherapy device of claim 3, wherein the expandable member is configured to expand separately from the plurality of off-set radiation delivery lumens.

14. A brachytherapy device for facilitating asymmetrical irradiation of a body cavity, comprising:
   an elongated shaft having a proximal end, a distal end, and a distal shaft portion proximal to the distal end; and
   an expandable member coupled to the elongated shaft to define an expandable volume at the distal shaft portion, the elongated shaft including:
      a central radiation delivery lumen having a central treatment portion located within the expandable volume,
      a plurality of off-set radiation delivery lumens, each off-set radiation delivery lumen of the plurality of off-set radiation delivery lumens having a respective off-set treatment portion radially off-set from the central treatment portion within the expandable volume, wherein the plurality of off-set radiation delivery lumens are configured to expand away from the central radiation delivery lumen, the central radiation delivery lumen and each off-set delivery lumen of the plurality of off-set radiation delivery lumens being respectively configured to receive a radiation source and guide the radiation source into the respective treatment portion, an inflation lumen coupled in fluid communication with the expandable volume defined by the expandable member, wherein the expandable member is configured to be spaced apart from the plurality of off-set radiation delivery lumens when the plurality of off-set radiation delivery lumens are expanded, and a cap located on the distal shaft portion, and a distal end of each of the off-set radiation delivery lumens is secured in the cap.

15. The brachytherapy device of claim 14, wherein each respective off-set radiation delivery lumen is configured to slidably hold the radiation source at a selected dwell position within the respective off-set treatment portion.

16. The brachytherapy device of claim 14, wherein the central radiation delivery lumen is configured to slidably hold the radiation source at a selected dwell position within the central treatment portion.

17. The brachytherapy device of claim 14, wherein each respective off-set treatment portion and the central treatment portion extends longitudinally across the expandable volume defined by the expandable member.

18. The brachytherapy device of claim 14, wherein each respective off-set treatment portion and the central treatment portion is located at a respective fixed position relative to a central longitudinal axis of the elongated shaft.

19. The brachytherapy device of claim 14, wherein each of the plurality of off-set radiation delivery lumens, the central radiation delivery lumen, and the inflation lumen has a respective proximal portion that extends proximally from the proximal end of the elongated shaft.

20. The brachytherapy device of claim 19, wherein at least the respective proximal portion of each of the plurality of off-set radiation delivery lumens, the central radiation delivery lumen, and the inflation lumen is flexible to facilitate movement of the respective proximal portion relative to the elongated shaft.

21. The brachytherapy device of claim 14, comprising three off-set treatment portions equally disposed around the central treatment portion.

22. The brachytherapy device of claim 14, comprising multiple off-set treatment portions equally disposed around the central treatment portion.

23. The brachytherapy device of claim 14, wherein the expandable member is configured to expand separately from the plurality of off-set radiation delivery lumens.

* * * * *